US011173106B2

(12) United States Patent
Fevola et al.

(10) Patent No.: US 11,173,106 B2
(45) Date of Patent: *Nov. 16, 2021

(54) COMPOSITIONS COMPRISING A SUPERHYDROPHILIC AMPHIPHILIC COPOLYMER AND A MICELLAR THICKENER

(75) Inventors: Michael J. Fevola, Belle Mead, NJ (US); Frank C. Sun, Branchburg, NJ (US); Joseph J. LiBrizzi, Hillsborough, NJ (US); Joseph B. Gardner, Somerset, NJ (US); Russel M. Walters, Philadelphia, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 558 days.

This patent is subject to a terminal disclaimer.

(21) Appl. No.: 12/574,895

(22) Filed: Oct. 7, 2009

(65) Prior Publication Data

US 2011/0081309 A1   Apr. 7, 2011

(51) Int. Cl.
 *A61K 8/86*  (2006.01)
 *A61K 8/85*  (2006.01)
 *A61Q 19/10*  (2006.01)
 *A61Q 19/00*  (2006.01)
 *A61K 8/73*  (2006.01)

(52) U.S. Cl.
 CPC ............... *A61K 8/86* (2013.01); *A61K 8/732* (2013.01); *A61K 8/85* (2013.01); *A61Q 19/00* (2013.01); *A61Q 19/10* (2013.01); *A61K 2800/48* (2013.01)

(58) Field of Classification Search
 CPC . A61K 8/86; A61K 8/732; A61K 8/85; A61K 2800/48; A61Q 19/00; A61Q 19/10
 See application file for complete search history.

(56) References Cited

U.S. PATENT DOCUMENTS

| | | |
|---|---|---|
| 2,661,349 A | 12/1953 | Caldwell |
| 2,736,678 A | 2/1956 | Olix |
| 2,868,781 A | 1/1959 | Gaertnervanr |
| 4,011,392 A | 3/1977 | Rudolph et al. |
| 4,028,290 A * | 6/1977 | Reid .............................. 524/768 |
| 4,035,235 A | 7/1977 | Richards |
| 4,061,610 A | 12/1977 | Glowaky et al. |
| 4,100,342 A | 7/1978 | Finley |
| 4,110,263 A | 8/1978 | Lindemann |
| 4,125,064 A | 11/1978 | Ackeret |
| 4,186,113 A | 1/1980 | Verdicchio |
| 4,215,064 A | 7/1980 | Lindemann |
| 4,233,192 A | 11/1980 | Lindemann |
| 4,239,592 A | 12/1980 | Gaspar |
| 4,332,935 A | 6/1982 | Fischer |
| 4,372,869 A | 2/1983 | Lindemann |
| 4,380,637 A | 4/1983 | Lindemann et al. |
| 4,382,036 A | 5/1983 | Lindemann |
| 4,387,221 A | 6/1983 | Tessier |
| 4,443,362 A | 4/1984 | Guth |
| 4,613,407 A | 9/1986 | Huchette |
| 4,617,414 A | 10/1986 | Lukenbach |
| 4,663,159 A | 5/1987 | Brode, II |
| 4,726,915 A | 2/1988 | Verdicchio |
| 4,734,239 A | 3/1988 | Diamantoglou |
| 4,845,152 A | 7/1989 | Palmer |
| 4,876,336 A | 10/1989 | Solarek |
| 4,906,744 A | 3/1990 | Peuscher |
| 4,964,953 A | 10/1990 | Solarek et al. |
| 4,977,252 A | 12/1990 | Chiu |
| 4,981,959 A | 1/1991 | Diamantoglou |
| 5,008,385 A | 4/1991 | Diamantoglou |
| 5,009,880 A | 4/1991 | Grollier et al. |
| 5,354,559 A | 10/1994 | Morehouse |
| 5,378,491 A | 1/1995 | Stanley et al. |
| 5,407,919 A | 4/1995 | Brode |
| 5,496,861 A | 3/1996 | Rouse et al. |
| 5,583,214 A | 12/1996 | Partain, III |
| 5,587,412 A | 12/1996 | Borchers et al. |
| 5,595,631 A | 1/1997 | Tsai |
| 5,672,699 A | 9/1997 | Billmers et al. |
| 5,684,141 A | 11/1997 | Schrell |
| 5,720,978 A | 2/1998 | Morehouse |
| 5,731,430 A | 3/1998 | Fuertes |
| 5,776,476 A | 7/1998 | Billmers |
| 5,780,616 A | 7/1998 | Fornasari |
| 5,783,200 A | 7/1998 | Motley et al. |

(Continued)

FOREIGN PATENT DOCUMENTS

| | | |
|---|---|---|
| AU | 607071 B2 | 0/0000 |
| DE | 102006034531 A | 1/2008 |

(Continued)

OTHER PUBLICATIONS

Jeon et al. Studies of Starch Esterification: Reactions with Alkenylsuccinates in Aqueous Slurry Systems. Starch 1999, 51(2-3):90-93.*
Janule. The dynamics of surface tension. Europian Coating Journal, 2005, 7(8):24. (Year: 2005).*
Franses et al. Techniques to measure dynamic surface tension. Current Opinion in Colloid & Interface Science, 1996, 1(2):296:303. (Year: 1996).*
Ogino e al., Reduction of Surface Tension by Novel Polymer Surfactants. Langmuir 1990, 6:1330. (Year: 1990).*
Kim et al. Europhys. Lett., 1993, 24 (31):229-234 (Year: 1993).*
Definition from Glossary of Basic Terms in Polymer Science, A.D. Jenkins et al., *Pure Appl. Chem.* 1996 68, 2287-2311.
Sagarin, Cosmetics, Science and Technology, $2^{nd}$ Edition, vol. 1, p. 32-43 (1972).

(Continued)

*Primary Examiner* — Robert A Wax
*Assistant Examiner* — Olga V. Tcherkasskaya
(74) *Attorney, Agent, or Firm* — Laura A. Donnelly

(57) ABSTRACT

Provided are healthcare compositions comprising a superhydrophilic amphiphilic copolymer, a micellar thickener, and a cosmetically-acceptable or pharmaceutically-acceptable carrier. Also, provided are methods of cleansing or treating a mammal by applying healthcare compositions of the present inventions to the mammalian body.

7 Claims, 1 Drawing Sheet

(56) References Cited

U.S. PATENT DOCUMENTS

| | | | |
|---|---|---|---|
| 5,795,397 A | 8/1998 | Shi et al. | |
| 5,797,984 A | 8/1998 | Billmers | |
| 5,851,300 A | 12/1998 | Linhart | |
| 5,932,639 A | 8/1999 | Eden et al. | |
| 5,954,883 A | 9/1999 | Nagle | |
| 5,969,090 A | 10/1999 | Mandeville, III et al. | |
| 6,033,647 A * | 3/2000 | Touzan et al. | 424/45 |
| 6,083,492 A | 7/2000 | Modi | |
| 6,103,885 A * | 8/2000 | Batelaan et al. | 536/18.7 |
| 6,123,738 A | 9/2000 | Childers | |
| 6,277,186 B1 | 8/2001 | Shi et al. | |
| 6,280,515 B1 * | 8/2001 | Lydzinski et al. | 106/122 |
| 6,369,019 B1 | 4/2002 | Gordon | |
| 6,369,117 B1 * | 4/2002 | Dubief et al. | 516/55 |
| 6,387,853 B1 | 5/2002 | Dawson | |
| 6,495,679 B1 | 12/2002 | Tanaka | |
| 6,517,678 B1 * | 2/2003 | Shannon et al. | 162/177 |
| 6,521,088 B1 | 2/2003 | Richardson et al. | |
| 6,562,172 B1 | 5/2003 | Kamen | |
| 6,566,516 B1 | 5/2003 | Sunamoto et al. | |
| 6,805,874 B1 | 10/2004 | Lutz et al. | |
| 6,905,694 B1 * | 6/2005 | Modi | 424/401 |
| 6,939,536 B2 * | 9/2005 | Chen et al. | 424/70.1 |
| 7,157,414 B2 | 1/2007 | Librizzi | |
| 7,157,573 B2 | 1/2007 | Buwalda et al. | |
| 7,186,823 B2 | 3/2007 | Käki et al. | |
| 7,285,647 B2 * | 10/2007 | Barbeito | A61K 8/604 536/18.3 |
| 7,417,020 B2 * | 8/2008 | Fevola et al. | 510/475 |
| 7,470,657 B2 * | 12/2008 | Guillou et al. | 510/475 |
| 7,541,320 B2 | 6/2009 | Dabkowski et al. | |
| 7,829,600 B1 | 11/2010 | Trksak | |
| 8,030,262 B2 | 10/2011 | Walters et al. | |
| 8,258,250 B2 | 9/2012 | Fevola et al. | |
| 8,399,590 B2 | 3/2013 | Gardner et al. | |
| 2002/0006389 A1 | 1/2002 | Restle et al. | |
| 2002/0123624 A1 | 9/2002 | Qiao et al. | |
| 2002/0123625 A1 | 9/2002 | Polovsky et al. | |
| 2002/0132309 A1 | 9/2002 | Bazin | |
| 2002/0143160 A1 | 10/2002 | Sunamoto | |
| 2002/0192280 A1 * | 12/2002 | Hunter et al. | 424/465 |
| 2003/0031775 A1 | 2/2003 | Altieri et al. | |
| 2003/0037894 A1 * | 2/2003 | Shannon et al. | 162/158 |
| 2003/0044490 A1 | 3/2003 | Qi et al. | |
| 2003/0059391 A1 * | 3/2003 | L'Alloret | 424/70.11 |
| 2003/0059392 A1 * | 3/2003 | L'Alloret | 424/70.11 |
| 2003/0084818 A1 | 5/2003 | Pelley et al. | |
| 2003/0197773 A1 | 10/2003 | Kaeding et al. | |
| 2003/0207038 A1 | 11/2003 | Han et al. | |
| 2004/0151681 A1 | 8/2004 | Busk | |
| 2004/0152857 A1 | 8/2004 | Ohnishi et al. | |
| 2004/0157755 A1 | 8/2004 | Niemiec | |
| 2004/0248761 A1 | 12/2004 | Booten | |
| 2005/0075256 A1 * | 4/2005 | Librizzi et al. | 510/130 |
| 2005/0079145 A1 | 4/2005 | Constantinides | |
| 2005/0118248 A1 | 6/2005 | Grinberg et al. | |
| 2005/0164896 A1 | 7/2005 | Dabkowski | |
| 2005/0233002 A1 | 10/2005 | Trubiano et al. | |
| 2005/0277768 A1 | 12/2005 | Buwalda | |
| 2006/0134047 A1 * | 6/2006 | Bakeev et al. | 424/70.13 |
| 2006/0162092 A1 | 7/2006 | Harrison | |
| 2006/0225855 A1 | 10/2006 | Ladret | |
| 2006/0280714 A1 | 12/2006 | Maningat | |
| 2007/0025979 A1 | 2/2007 | Pryzdial | |
| 2007/0122482 A1 | 5/2007 | Holm | |
| 2007/0136954 A1 | 6/2007 | Penninger | |
| 2007/0137523 A1 | 6/2007 | Vestin | |
| 2007/0148431 A1 | 6/2007 | Sauer | |
| 2007/0185281 A1 | 8/2007 | Song et al. | |
| 2007/0259797 A1 | 11/2007 | Fevola | |
| 2008/0003192 A1 * | 1/2008 | Modi | 424/70.13 |
| 2008/0199420 A1 | 8/2008 | Wendel | |
| 2008/0223536 A1 | 9/2008 | Horst | |
| 2008/0255276 A1 | 10/2008 | Jetzinger et al. | |
| 2008/0312341 A1 | 12/2008 | Futterer | |
| 2009/0019646 A1 | 1/2009 | Walters et al. | |
| 2009/0088565 A1 * | 4/2009 | Schick et al. | 536/123.1 |
| 2009/0175804 A1 | 7/2009 | Jennings et al. | |
| 2009/0214447 A1 | 8/2009 | Jennings et al. | |
| 2009/0277355 A1 | 11/2009 | Pawlowska | |
| 2010/0305271 A1 | 12/2010 | Mentink et al. | |
| 2010/0330376 A1 | 12/2010 | Trksak et al. | |
| 2011/0021734 A1 | 1/2011 | Samaranayake | |
| 2011/0081309 A1 | 4/2011 | Fevola | |
| 2011/0081310 A1 | 4/2011 | Fevola | |
| 2011/0082065 A1 | 4/2011 | Fevola | |
| 2011/0082105 A1 | 4/2011 | Fevola | |
| 2011/0082290 A1 | 4/2011 | Gardner | |
| 2011/0110989 A1 | 5/2011 | Simonnet et al. | |
| 2011/0124746 A1 | 5/2011 | Trksak et al. | |
| 2011/0287165 A1 | 11/2011 | Shi | |
| 2013/0172545 A1 | 7/2013 | Gardner et al. | |
| 2014/0265007 A1 | 9/2014 | Bruning et al. | |

FOREIGN PATENT DOCUMENTS

| | | |
|---|---|---|
| EP | 0542236 A1 | 0/0000 |
| EP | 1743693 A1 | 0/0000 |
| EP | 0703243 A | 3/1996 |
| EP | 1584370 A | 10/2005 |
| EP | 2018890 A | 1/2009 |
| EP | 2018890 A2 * | 1/2009 |
| JP | 02006501 A | 1/1990 |
| JP | 04363301 A | 12/1992 |
| JP | 05301906 A | 11/1993 |
| JP | 08183805 A | 7/1996 |
| JP | 2007239156 A | 9/2007 |
| WO | WO 09/016663 A1 | 0/0000 |
| WO | WO 2000/042076 A | 7/2000 |
| WO | 2002/098375 A | 12/2002 |
| WO | 2007/008066 A | 1/2007 |
| WO | 2011/042379 A | 4/2011 |

OTHER PUBLICATIONS

The International Cosmetic Ingredient Dictionary and Handbook, eds. Wenninger and Mc Ewen, pp. 1656-1661, 1626, and 1654-1655 (The Cosmetic, Toiletry, and Fragrance Assoc., Washington, D.C., 7. sup. Th Edition, 1997).

Handbook of Applied Surface and Colloid Chemistry, vol. 2, Holmberg, K., Ed.; John Wiley & Sons: Chicester, U.K., 2002, pp. 222-223.

Axisymmetric Drop Shape Analysis (ADSA), Neumann A.W., Spelt J.K., Eds. New York: Marcel Dekker Inc., 1996, Ch. 10; Hoorfar M., Neumann, A.W. Adv. Coll. and Interface Sci 2006, 121(1-3), 25-49.

European Search Report for EP Application No. 09177151.9; dated Apr. 1, 2010.

International Search Report for PCT Application No. EP2010/064711; dated Nov. 4, 2010.

Office Action dated Dec. 16, 2011 for U.S. Appl. No. 12/575,151.

Restriction Requirement dated Jan. 21, 2011 for U.S. Appl. No. 12/574,886.

Office Action dated Jan. 19, 2012 for U.S. Appl. No. 12/574,886.

Anna Jonhed et al., "Phase and Gelation Behavior or 2-Hydroxy-3-(N,N-dimethyl-N-dodecylammonium)propyloxy Starches", Starch/Starke 55 (2003) 569-575.

Ezell et al., "Amino Acid-Based, Amphiphilic Block Copolymers and Statistical Terpolymers with pH- and Salt-Responsive Behavior in Aqueous Media", *Polymer Preprints* 2005, 46(2), 499-500.

Handbook of Hydrocolloids, edited by G. O. Phillips and P. A. Williams, Chapter 3, *Starch*, P. Murphy, pp. 41-46, 2000, CRC Press, New York.

Chi et al., "Synthesis of dodecenyl succinic anhydride (DDSA) corn starch", Food Research International (2007) 40:232-238.

Database GNPD [Online] MINTEL; Sep. 2002, "Neutrogena Visibly Refined Facial Care Products—Pore refining facial wash", XP002713424, Database accession No. 166430 *Ingredients *.

Database GNPD [Online] MINTEL; Aug. 2006, "Essential starter program for oily acne prone skin", XP002713425, Database accession No. 579017 *Products description Acne treatment fluid ingredients *.

(56) References Cited

OTHER PUBLICATIONS

Database GNPD [Online] MINTEL; Sep. 2007, "03 Day lotion". XP002713426, Database accession No. 779648 *Product description Ingredients *.
Database GNPD [Online] MINTEL; Dec. 2003, "Oil Control Lightening Foam", XP002713922, Database accession No. 241643 *Product description Ingredients*.
Database GNPD [Online] MINTEL; Nov. 2005, "Shampoo 1", XP002713923, Database accession No. 409316 *Ingredients*.
Database GNPD [Online] MINTEL; Oct. 2008, "Facial Cleansing cream", XP002713924, Database accession No. 984142 *Product description Ingredients*.
Wesslen et al., "Synthesis of amphiphilic amylose and starch derivatives", Carbohydrates Polymers (2002) 47:303-311.
Brooks et al., "Saccharide Analysis of Corn Syrup solids and Maltodextrins Using High-Performance Liquid Chromatography", *Cereal Chem.* (1987) 64(4):253-255.
Striegel et al., Modern Size-Exclusion Liquid Chromatography, $2^{nd}$ Edition (2009) 12.4 Select Applications of Aqueous Sec, p. 327.
"Molecular structure," [online] Native Starches—Molecular Structure—Cargill Food Ingredients, Cargill Corporate [retrieved Mar. 23, 2015], Retrieved from the Internet: http://www.cargillfoods.com/na/en/products/starches-derivatives/molecular-structure/index.jsp. (pp. 1-2).
Yanli Xie et al., "Effect of microwave treatment on the physicochemical properties of potato starch granules," Chemistry Central Journal [online], published Jul. 8, 2013, 7:113. Retrieved from the Internet: http://journal.chemistrycentral.com/content/7/1/113. (pp. 1-6).

\* cited by examiner

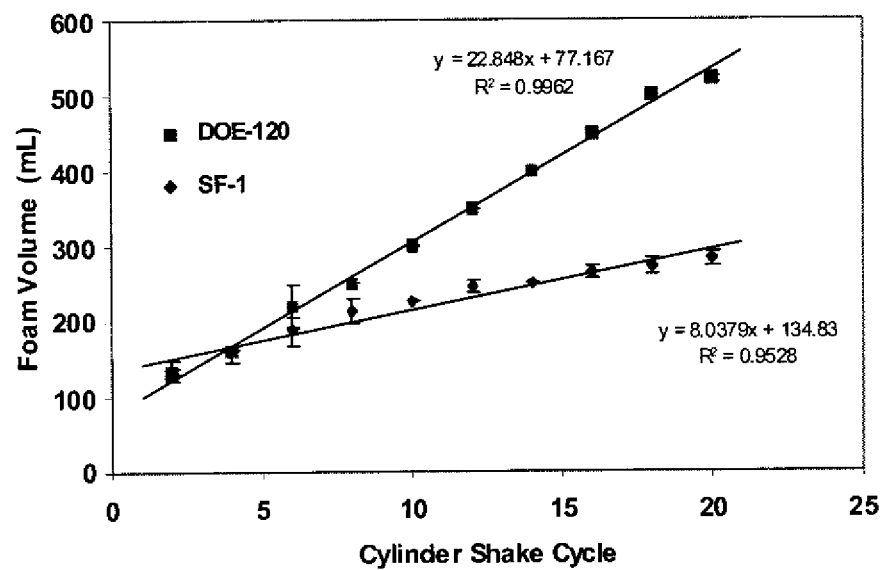

COMPOSITIONS COMPRISING A SUPERHYDROPHILIC AMPHIPHILIC COPOLYMER AND A MICELLAR THICKENER

FIELD OF INVENTION

The present invention relates to compositions comprising superhydrophilic amphiphilic copolymers and, in particular, compositions comprising superhydrophilic amphiphilic copolymers that are useful in healthcare applications and have relatively low irritation and high flash-foaming associated therewith.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to use combinations and levels of surfactants sufficient to achieve relatively high foam volume and/or foam stability.

However, as is recognized in the art, synthetic detergents tend to be irritating to the skin and eyes. Thus, as levels of such detergents are increased in attempts to increase cleansing and foaming properties associated with certain compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating), with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance. Yet another approach described in, Librizzi et al., (in United States Published Patent Application US20050075256 A1) discusses the use of a composition including both a hydrophobically modified polymer and a surfactant to provide low irritation cleansing composition.

Still another approach to producing mild cleansing compositions is to use polymerized surfactants having a relatively low degree-of-polymerization and at least about 10 mol % amphiphilic repeat units. See U.S. Pat. No. 7,417,020.

However, while improvements have made been in mildness, the inventors have recognized that additional improvements in mildness are desirable, particularly improvements in both mildness and the ability of compositions to provide exceptional so-called "flash foam," i.e., the ability to form a high volume of foam with relatively low amount of energy input.

BRIEF DESCRIPTION OF THE DRAWING

FIG. 1 is a graph of the foam generation rate of a composition of the present invention and a comparative example.

SUMMARY OF THE INVENTION

The present invention provides compositions, including healthcare and non-healthcare compositions, that overcome the disadvantages of the prior art and have relatively low irritation properties associated therewith. In particular, applicants have discovered that certain polymeric materials may be used to great advantage to produce compositions having low irritation associated therewith and, in certain embodiments, combinations of additional beneficial aesthetic and other properties. In addition, applicants have discovered that in certain embodiments the polymeric materials of the present invention may be combined with micellar thickeners to produce compositions that exhibit significant and unexpected amounts of flash foaming.

According to one aspect, the present invention provides compositions comprising a superhydrophilic amphiphilic copolymer and a carrier. Such compositions may include healthcare and/or non-healthcare compositions.

According to another aspect, the present invention provides compositions comprising a superhydrophilic amphiphilic copolymer, a micellar thickener, and a carrier.

DESCRIPTION OF PREFERRED EMBODIMENTS

All percentages listed in this specification are percentages by weight, unless otherwise specifically mentioned.

As used herein, the term "healthcare" refers to the fields of personal care and medical care including, but not limited to, infant care, oral care, sanitary protection, skin care, including the treatment of adult or infant skin to maintain the health of the skin, improve the health of the skin, and/or improve the appearance of the skin, wound care, including the treatment of a wound to assist in the closure or healing of a wound, and/or to reduce the pain or scarring associated with the wound, women's health, including the treatment of tissue in the internal or external vaginal area and/or breast, maintaining or improving the health of such tissue or skin, repairing such tissue or skin, reducing irritation of such tissue or skin, maintaining or improving the appearance of such tissue or skin, and improving or enhancing sexual function associated with such tissue or skin, and the like.

As used herein, the term "superhydrophilic amphiphilic copolymer," ("SAC") is defined as a copolymer that may be represented by the following general structure:

wherein an "SRU" is a superhydrophilic repeat unit as defined herein, an "ARU" is an amphiphilic repeat unit as defined herein, an "HRU" is a hydrophilic repeat unit as defined herein, wherein s≥2, a>0, h≥0, and the total number of repeat units, s+a+h is between 4 and about 1000. The term "between," when used herein to specify a range such as "between 4 and about 1000," is inclusive of the endpoints, e.g. "4" and "about 1000." The total number of repeat units in the SAC is based on the weight-average molecular weight ($M_w$) of the SAC; thus the number of repeat units, as discussed herein are "weight average" as well. Further, all molecular weights described herein are in the units of Daltons (Da). As will be recognized by one of skill in the art, the pattern of repeat units (SRUs, ARUs, HRUs) incorporated in SACs of the present invention are generally random; however, they may also have alternating, statistical, or blocky incorporation patterns. In addition, SAC architectures may be linear, star-shaped, branched, hyperbranched, dendritic, or the like.

Those of skill in the art will recognize that total number of repeat units in a SAC (SRUs+ARUs+HRUs, i.e. s+a+h in the above formula) is synonymous with the term "degree of polymerization" ("DP") of the SAC.

A "repeat unit" as defined herein and known the art is the smallest atom or group of atoms (with pendant atoms or groups, if any) comprising a part of the essential structure of a macromolecule, oligomer, block, or chain, the repetition of which constitutes a regular macromolecule, a regular oligomer molecule, a regular block, or a regular chain (definition from Glossary of Basic Terms in Polymer Science, A. D. Jenkins et al. *Pure Appl. Chem.* 1996 68, 2287-2311.) As will be recognized by those of skill in the art in light of the description herein and knowledge of the art, the backbone of a polymer derived from ethylenically-unsaturated monomers comprises repeat units including one or two, or in the case of alternating polymers four, carbon atoms that were unsaturated in the monomers prior to polymerization, and any pendant groups of such carbons. For example, polymerization of an ethylenically-unsaturated monomer of the formula: $(A)(Y)C=C(B)(Z)$ will generally result in a polymer comprising repeat units of the formula:

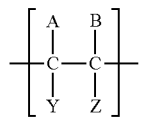

comprising the two previously unsaturated carbons of the monomer and their pendant groups (examples of which are described herein below, for example in the descriptions of SRUs, ARUs, and HRUs.) However, if the pendant groups of the two carbons are the same such that, for example in the formula above, A-C—Y and B—C—Z are the same moiety, then each of such one carbon units and its pendant groups (A-C—Y or B—C—Z, being the same) are considered to be the repeat unit comprising only one previously unsaturated carbon from the monomer (e.g. the repeat unit of a homopolyer derived from ethylene, $H_2C=CH_2$ is [—[$CH_2$]—] not [—[$CH_2CH_2$]—]. With regard only to alternating copolymers, which as known in the art are defined as those polymers in which the repeat units derived from the two comonomers alternate consistently throughout the polymer (as opposed to the random polymerization of co-monomers to form a polymer in which repeat units derived from the two monomers are randomly linked throughout the polymer or the block copolymerization of comonomers to form non-alternating blocks of repeat units derived from the two monomers), the repeat unit is defined as the unit derived from one of each of the co-monomers comprising four carbons that were previously ethylenically-unsaturated in the two comonomers prior to polymerization. That is, maleic anhydride and vinyl methyl ether are used in the art to form an alternating copolymer, poly(maleic anhydride-alt-vinyl methyl ether) having repeat units of the structure:

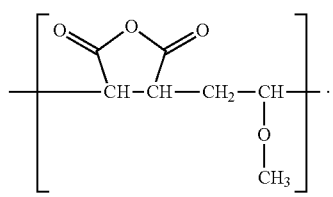

For saccharide-based polymers whose backbone is formed by linking sugar rings, the repeat unit generally comprises the sugar ring and pendant groups (as shown herein below, for example in the descriptions of SRUs, ARUs, and HRUs.) Examples of such repeat units also include sugar ring repeat units with pendant sugar rings, for example, Galactomannans are polysaccharides comprised of a mannose (monosaccharide-based) backbone. Pending from some but not all of the mannose groups in the backbone (and arranged in either a random or block fashion) are pendant galactose groups. As will be readily understood by one skilled in the art, this structure is best described as having, two repeat units, mannose and mannose-galactose.

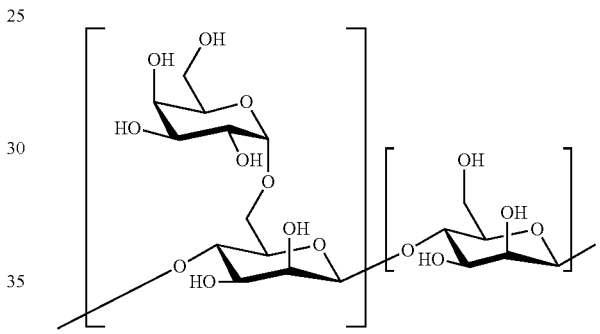

For alternating saccharide-based polymers, then the repeat unit is the two sugar rings derived from the alternating sugar-based monomers and their pendant groups. For example, Hyaluronan is an alternating saccharide copolymer derived from two saccharides, D-glucuronic acid and D-N-acetylglucosamine that alternate to give a disaccharide repeat units.

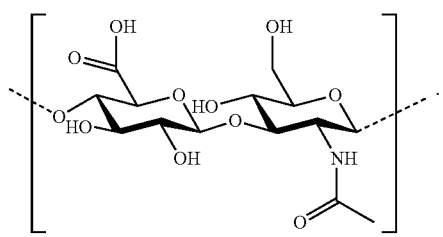

A "hydrophobic moiety" is hereby defined as a nonpolar moiety that contains at least one of the following: (a) a carbon-carbon chain of at least four carbons in which none of the four carbons is a carbonyl carbon or has a hydrophilic moiety bonded directly to it; (b) two or more alkyl siloxy groups (—[Si(R)$_2$—O]—); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly(oxybutylene), poly(dimethylsiloxane), fluorinated hydrocarbon groups containing a carbon chain of at least four carbons in which none of the four carbons has a hydrophilic moiety bonded directly to it, and the like.

As used herein, the term "hydrophilic moiety," is any anionic, cationic, zwitterionic, or nonionic group that is polar. Nonlimiting examples include anionics such as sulfate, sulfonate, carboxylic acid/carboxylate, phosphate, phosphonates, and the like; cationics such as: amino, ammonium, including mono-, di-, and trialkylammonium species, pyridinium, imidazolinium, amidinium, poly(ethyleneiminium), and the like; zwitterionics such as ammonioalkylsulfonate, ammonioalkylcarboxylate, amphoacetate, and the like; and nonionics such as hydroxyl, sulfonyl, ethyleneoxy, amido, ureido, amine oxide, and the like.

As used herein, the term "superhydrophilic repeat unit," ("SRU") is defined as a repeat unit that comprises two or more hydrophilic moieties and no hydrophobic moieties. For example, SRUs may be derived from ethylenically-unsaturated monomers having two or more hydrophilic moieties and no hydrophobic moieties, including repeat units of the general formulae:

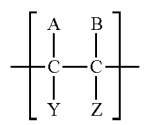

wherein A, B, Y, and Z collectively include at least two hydrophilic moieties and no hydrophobic moieties; or

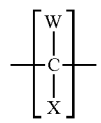

wherein W and X collectively include at least two hydrophilic moieties. Illustrative examples of such SRUs include, but are not limited to, those derived from superhydrophilic monomers described herein and the like, such as:

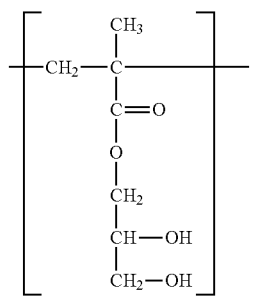

which is derived from glyceryl methacrylate; or others such as

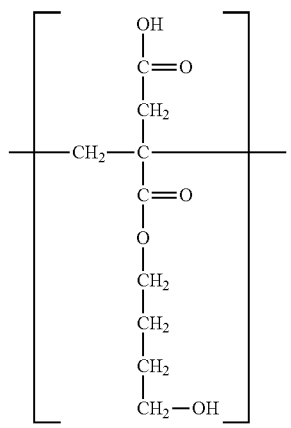

which is derived from 4-Hydroxybutyl itaconate; and the like.

Other examples of SRUs include saccharide-based repeat units including repeat units derived from fructose, glucose, galactose, mannose, glucosamine, mannuronic acid, guluronic acid, and the like, such as:

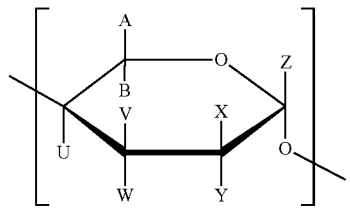

wherein A, B, U, V, W, X, Y, and Z collectively include at least two hydrophilic moieties and no hydrophobic moieties, one example of which includes

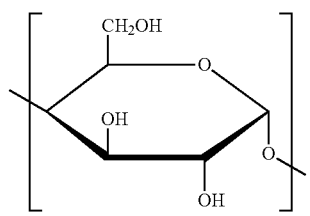

which is a α(1→4)-D-glucose SRU; or

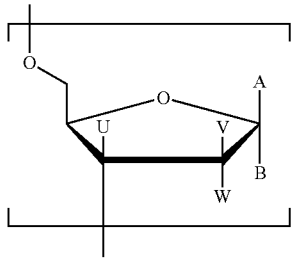

wherein A, B, U, V, and W collectively include at least two hydrophilic moieties and no hydrophobic moieties, one example of which includes

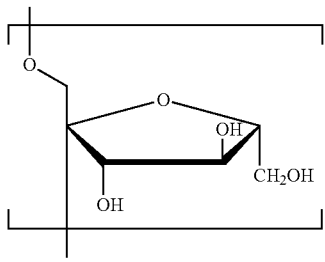

a β(2→1)-D-fructose SRU; and the like. As will be recognized by those of skill in the art, monosaccharide repeat units may be linked in various fashions, that is, through various carbons on the sugar ring e.g. (1→4), (1→6), (2→1), etc. Any of such linkages, or combinations thereof, may be suitable for use herein in monosaccharide SRUs, ARUs, or HRUs.

Other examples of SRUs include repeat units derived from amino acids, including, for example, repeat units of the formula:

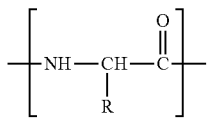

wherein R includes a hydrophilic repeat unit, examples of which include

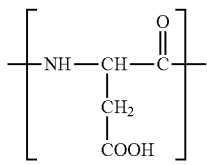

an aspartic acid SRU, and the like.

As used herein, the term "amphiphilic repeat unit," ("ARU") is defined as a repeat unit that comprises at least one hydrophilic moiety and at least one hydrophobic moiety. For example, ARUs may be derived from ethylenically-unsaturated monomers having at least one hydrophilic moiety and at least one hydrophobic moiety, including repeat units of the general formulae

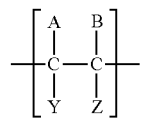

wherein A, B, Y, and Z collectively include at one hydrophilic moiety and at least one hydrophobic moiety; or

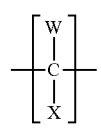

wherein W and X collectively include at one hydrophilic moiety and at least one hydrophobic moiety; examples of which include

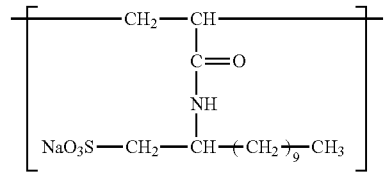

sodium 2-acrylamidododecylsulfonate amphiphilic repeat unit (ARU), and the like.

Other examples of ARUs include saccharide-based repeat units including repeat units derived from including repeat units derived from fructose, glucose, galactose, mannose, glucosamine, mannuronic acid, guluronic acid, and the like, such as:

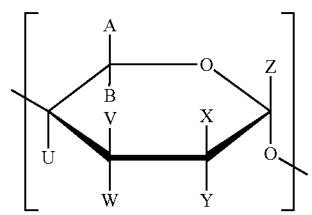

wherein A, B, U, V, W, X, Y, and Z collectively include at least one hydrophilic moiety and at least one hydrophobic moiety, or

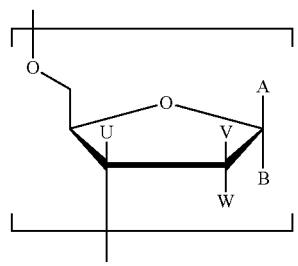

wherein A, B, U, V, and W collectively include at least one hydrophilic moiety and at least one hydrophobic moiety, examples of which include

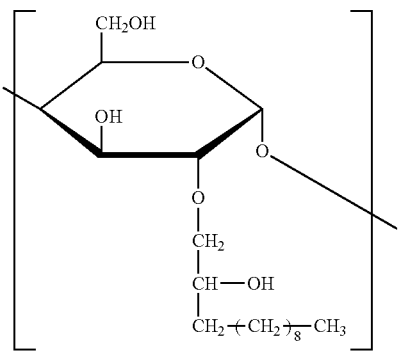

1,2-epoxydodecane modified α(1→4)-D-glucose ARU, and the like.

Other examples of ARUs include repeat units derived from amino acids, including, for example, repeat units of the formula:

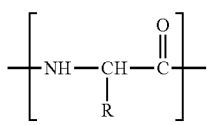

wherein R includes a hydrophobic group, examples of which include

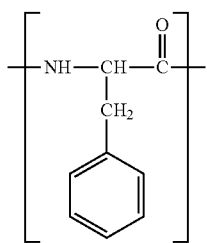

a phenylalanine ARU; and the like.

As will be readily understood by those of skill in the art, the term "hydrophilic repeat unit," ("HRU") is defined as a repeat unit that comprises one and only one hydrophilic moiety and no hydrophobic moieties. For example, HRUs may be derived from ethylenically-unsaturated monomers having one and only one hydrophilic moiety and no hydrophobic moieties, including repeat units of the general formulae

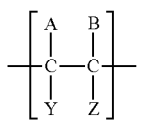

wherein A, B, Y, and Z collectively include one and only one hydrophilic moiety and no hydrophobic moieties; or

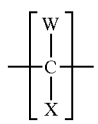

wherein W and X collectively include one and only one hydrophilic moiety and no hydrophobic moieties, examples of which include

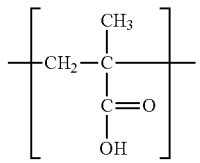

methacrylic acid hydrophilic repeat unit (HRU); and the like.

Other examples of HRUs include saccharide-based repeat units including repeat units derived from fructose, glucose, galactose, mannose, glucosamine, mannuronic acid, guluronic acid, and the like, such as:

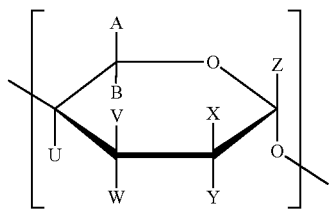

wherein A, B, U, V, W, X, Y, and Z collectively include one and only one hydrophilic moiety and no hydrophobic moieties, or

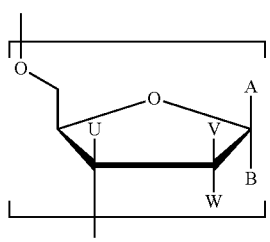

wherein A, B, U, V, and W collectively include one and only one hydrophilic moiety and no hydrophobic moieties. One example of saccharide-based hydrophilic repeat unit includes methylcellulose HRU, (methyl-substituted poly[β(1→4)-D-glucose], DS=2.0)

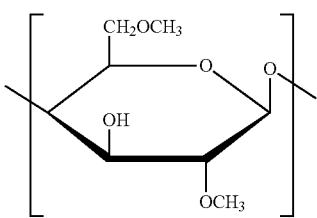

Other examples of HRUs include repeat units derived from amino acids, including, for example, repeat units of the formula:

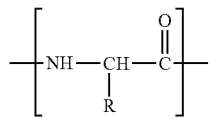

wherein R is neither a hydrophilic nor hydrophobic moiety, one example of which includes

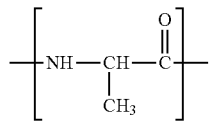

alanine HRU; and the like. As will be recognized by one of skill in the art, in any of the formulae herein, examples of moieties that are neither hydrophilic nor hydrophobic include hydrogen, $C_1$-$C_3$ alkyl, $C_1$-$C_3$ alkoxy, $C_1$-$C_3$ acetoxy, and the like.

As noted above, applicants have discovered unexpectedly that certain SACs are suitable for use in producing compositions having relatively low irritation and relatively high amounts of foam associated therewith. In certain other embodiments, wherein such SACs are in combination with micellar thickeners, the SACs are suitable for use in producing compositions that further exhibit relatively high amounts of flash foaming. According to certain preferred embodiments, applicants have discovered that SACs having a DP between 4 and about 1000 repeat units, exhibit such significant and unexpected combination of low-irritation and high foaming properties and are suitable for use in embodiments with micellar thickeners to exhibit high flash foaming. Examples of preferred SACs suitable for use in accord with such embodiments, include those having a DP of between 4 and about 500, more preferably 4 and about 200, more preferably 4 and about 100, more preferably 4 and about 50 repeat units. Other examples include those having a DP of between 5 and about 500, more preferably 5 and about 200, more preferably 5 and about 100, more preferably 5 and about 50 repeat units. Other examples include those having a DP of between 6 and about 200, more preferably 6 and about 100, more preferably 6 and about 50 repeat units. Other examples include those having a DP of between 7 and about 100, more preferably 7 and about 50 repeat units.

According to certain embodiments, applicants have further discovered that certain SACs are capable of forming compositions having relatively low "Dynamic Surface Tension Reduction Time" (that is, the time required to reduce surface tension of pure water from 72 mN/m to 55 mN/m, "$t_{\gamma=55}$", associated with a particular composition, which value is measured conventionally via the prop Shape Analysis Test ("DSA Test") described in further detail in the Examples below) and are preferred for use in compositions having significant and unexpected combinations of low-irritation and high foaming properties, and in certain embodiments high flash-foaming, as compared to comparable compositions. According to certain preferred embodiments, the SACs of the present invention have a $t_{\gamma=55}$ of about 120 seconds (s) or less. In certain more preferred embodiments, the SACs of the present invention have a $t_{\gamma=55}$ of about 75 seconds or less, more preferably about 50 or less, more preferably about 45 or less.

Applicants have further discovered that while a variety of conventional polymers, including ones having higher DPs and/or more ARUs than SACs of the present invention, are designed specifically to increase the viscosity of a composition in small amounts, certain SACs of the present invention tend to have relatively small effect on the rheology of the compositions to which they are added. Accordingly, in certain embodiments, higher amounts of the present SACs may be added to more significantly reduce irritation, create relatively fast and copious foam, without producing a composition that is too viscous for effective personal use. In particular, suitable SACs include those having a solution viscosity (measured in accord with the "Solution Viscosity Test," described herein below and shown in the Examples) of about 9 centipoise (cP) or less. In certain more preferred embodiments, the SACs of the present invention have a solution viscosity of about 7 cps or less, more preferably about 4 cps or less, more preferably about 3 cps or less.

According to certain preferred embodiments, SACs suitable for use in the present invention exhibit a mole percent (mol %) of amphiphilic repeat units (amphiphilic mol %=(a/s+a+h)) of less than 10%. In certain preferred embodiments, such SACs include those having a mol % of ARUs of from about 0.1 to 9.9 mol %, more preferably from about 0.1 to about 9.4 mol %, more preferably from about 0.1 to about 8.5 mol %, and more preferably from about 0.1 to about 8.0 mol %. In certain preferred embodiments, the SACs include those having a mol % of ARUs of from about 0.5 to about 9.4 mol %, more preferably from about 0.5 to about 8.5 mol %, and more preferably from about 0.5 to about 8.0 mol %. In certain preferred embodiments, the SACs include those having a mol % of ARUs of from about 1 to about 8.5 mol %, and more preferably from about 1 to about 8.0 mol %.

The SACs of the present invention may be of any suitable molecular weight (provided the required DP is met). In certain preferred embodiments, the SAC has a weight average molecular weight from about 1000 grams/mol to about 200,000 grams/mol. In a preferred embodiment, the SAC has a weight average molecular weight of from about 1000 to about 100,000, more preferably from about 1,000 to about 75,000, more preferably from about 1,000 to about 50,000, more preferably from about 1,000 to about 25,000, and more preferably from about 1,000 to about 10,000, and more preferably from about 3,000 to about 10,000.

SACs suitable for use in the present invention include polymers of various chemical classifications and obtained via a variety of synthetic routes. Examples include polymers having a backbone that substantially comprises a plurality of carbon-carbon bonds, preferably essentially consists or consists only of carbon-carbon bonds and polymers having a backbone comprising a plurality of carbon-heteroatom bonds (as will be recognized by those of skill in the art, the backbone refers generally to the portion of repeat units in a polymer that is covalently bonded to adjacent repeat units (vs. "pendant groups").

Examples of synthetic routes for obtaining SACs of the present invention include copolymerization of (i) one or more ethylenically unsaturated amphiphilic comonomers with (ii) one or more ethylenically unsaturated superhydrophilic comonomers, and optionally, (iii) one or more ethylenically unsaturated hydrophilic comonomers. Nonlimiting examples of ethylenically unsaturated amphiphilic comonomers include those having the following structure:

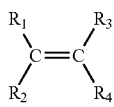

where $R_1=R_2=H$, $R_3=H$ or $CH_3$, and $R_4$ comprises Amphiphilic (Amphil) group, or where $R_1=R_2=H$, $R_3$ comprises a hydrophilic group (Hphil), and $R_4$ comprises hydrophobic group (Hphob), or where $R_1$, $R_3$ are independently H or $CH_3$, $R_2$ comprises Hphil, and $R_4$ comprises Hphob group, or where $R_1$, $R_4$ are independently H or $CH_3$, $R_3$ comprises Hphil, and $R_4$ comprises Hphob group, or where $R_2$, $R_3$ are independently H or $CH_3$, $R_1$ comprises Hphil, and $R_4$ comprises Hphob group examples of which include:

Anionic:

ω-alkeneoates: e.g. sodium 11-undecenoate

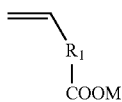

where $R_1$=any linear or branched carbon chain containing more than 5 carbon atoms and $M=H^+$, $NH_4^+$, or any Group IA alkali metal cation.

(Meth)acrylamidoalkylcarboxylates and (meth)acryloyloxyalkylcarboxylates: e.g. sodium 11-acrylamidoundecanoate, sodium 11-methacryloyloxyundecanoate

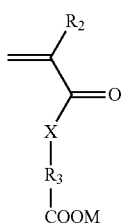

where $R_2=H$ or $CH_3$, $X=O$ or NH, $R_3$=any linear or branched carbon chain containing more than 5 carbon atoms and $M=H^+$, $NH_4^+$, or any Group IA alkali metal cation.

(Meth)acrylamidoalkylsulfonic acids: e.g. 2-acrylamidododecylsulfonic acid

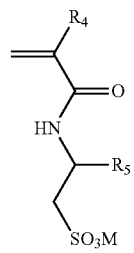

where $R_4=H$ or $CH_3$, $X=O$ or NH, $R_5$=any linear or branched carbon chain containing more than 5 carbon atoms and $M=H^+$, $NH_4^+$, or any Group IA alkali metal cation.

Allylalkylsulfosuccinates: e.g. sodium allyldodecylsulfosuccinate (TREM LF-40, Cognis)

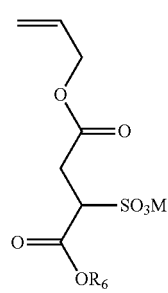

where $R_6$=any linear or branched carbon chain containing more than 5 carbon atoms and $M=H^+$, $NH_4^+$, or any Group IA alkali metal cation.

Cationic:

Quaternized aminoalkyl(meth)acrylamides and aminoalkyl(meth)acrylates: e.g. (3-methacrylamidopropyl)dodecyldimethylammonium chloride, (2-methacryloyloxyethyl)dodecyl dimethylammonium chloride

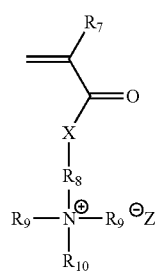

where $R_7=H$ or $CH_3$, $X=O$ or NH, $R_8$=any linear or branched carbon chain containing 5 or less carbon atoms, $R_9=H$, $CH_3$, $CH_2CH_3$ or $CH_2CH_2OH$, $R_{10}$=any linear or branched carbon chain containing more than 5 carbon atoms and Z=any Group VII-A halide anion, OR where $R_7=H$ or $CH_3$, $X=O$ or NH, $R_8$=any linear or branched carbon chain containing more than 5 carbon atoms, $R_9$, $R_{10}$ are independently H, $CH_3$, $CH_2CH_3$ or $CH_2CH_2OH$, and Z=any Group VII-A halide anion Quaternized vinylpyridines: e.g. (4-vinyl)dodecylpyridinium bromide

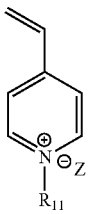

where $R_{11}$=any linear or branched carbon chain containing more than 5 carbon atoms and Z=any Group VII-A halide anion.

Alkyldiallylmethylammonium halides: e.g. diallyldodecylmethylammonium chloride

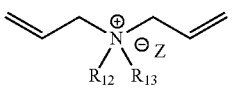

where $R_{12}$=H, $CH_3$ or $R_{13}$, $R_{13}$=any linear or branched carbon chain containing more than 5 carbon atoms and Z=any Group VII-A halide anion.

Zwitterionic:
Ammonioalkanecarboxylates:
e.g. 2-[(11-(N-methylacrylamidyl)undecyl)dimethylammonio]acetate

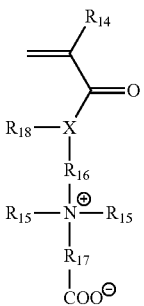

where $R_{14}$=H or $CH_3$, X=O or N, $R_{15}$=H, $CH_3$, $CH_2CH_3$ or $CH_2CH_2OH$, $R_{16}$=any linear or branched carbon chain more than 5 carbon atoms, $R_{17}$=any linear or branched carbon chain containing 5 or less carbon atoms, and $R_{18}$=H, $CH_3$, or nothing.

Ammonioalkanesulfonates: e.g. 3-[(11-methacryloyloxyundecyl)dimethylammonio]propanesulfonate

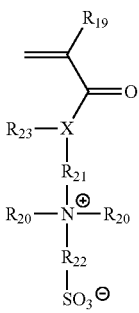

where $R_{19}$=H or $CH_3$, X=O or N, $R_{20}$=H, $CH_3$, $CH_2CH_3$ or $CH_2CH_2OH$, $R_{21}$=any linear or branched carbon chain more than 5 carbon atoms, $R_{22}$=any linear or branched carbon chain containing 5 or less carbon atoms, and $R_{23}$=H, $CH_3$, or nothing.

Nonionic:
ω-methoxypoly(ethyleneoxy)alkyl-α-(meth)acrylates:
e.g. ω-methoxypoly(ethyleneoxy)undecyl-α-methacrylate

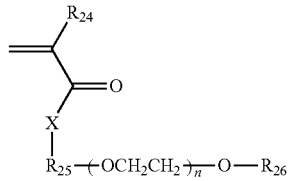

where $R_{24}$=H or $CH_3$, X=O, $R_{25}$=any linear or branched carbon chain more than 5 carbon atoms, n is an integer from about 4 to about 800, and $R_{26}$=any linear or branched carbon chain containing 5 or less carbon atoms ω-alkoxypoly(ethyleneoxy)-α-(meth)acrylates and ω-alkoxypoly(ethyleneoxy)-α-itaconates: e.g. steareth-20 methacrylate, ceteth-20 itaconate

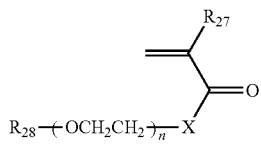

where $R_{27}$=H, $CH_3$, or $CH_2COOH$, X=O, $R_{28}$=any linear or branched carbon chain more than 5 carbon atoms, and n is an integer from about 4 to about 800

Nonlimiting examples of ethylenically unsaturated superhydrophilic comonomers include the following, and the like:

Nonionic:
glyceryl(meth)acrylate
sucrose mono(meth)acrylate, glucose mono(meth)acrylate tris(hydroxymethyl)acrylamidomethane, 1-(2-(3-(allyloxy)-2-hydroxypropylamino)ethyl)imidazolidin-2-one (Sipomer® WAM from Rhodia)

Anionic:
itaconic acid, hydrophilic derivatives thereof, and alkali metal salts thereof
crotonic acid, hydrophilic derivatives thereof, and alkali metal salts thereof
maleic acid, hydrophilic derivatives thereof, and alkali metal salts thereof.

Cationic:
2-(meth)acryloyloxy-N-(2-hydroxyethyl)-N,N-dimethylethylammonium chloride, 3-(meth)acrylamido-N-(2-hydroxyethyl)-N,N-dimethylpropylammonium chloride, 3-(meth)acrylamido-N,N-bis(2-hydroxyethyl)-N-methylpropylammonium chloride, N-(2-(bis(2-hydroxyethyl)amino)ethyl)(meth)acrylate, N-(3-(bis(2-hydroxyethyl)amino)propyl)(meth)acrylamide, N-(2-((meth)acryloyloxy)ethyl)-N,N,N',N',N'-pentamethylethane-1,2-diammonium dichloride Zwitterionic:
3-[(3-(meth)acrylamidopropyl)dimethylammonio]propanesulfonate, 3-(3-(meth)acrylamidopropyldimethylammonio)propionate, 3-(3-(meth)acrylamidopropyldimethylammonio)acetate, 2-(meth)acryloyloxyethylphosphorylcholine, and the like Nonlimiting examples of optional ethylenically unsaturated hydrophilic comonomers include the following, and the like:

Nonionic:
  e.g. acrylamide, N,N-dimethylacrylamide, N-vinylformamide, hydroxyethyl(meth)acrylate, (meth)acrylamidoethylethyleneurea, ω-methoxypoly(ethyleneoxy)-α-(meth)acrylate, and the like Anionic:
  acrylic acid, β-carboxyethyl acrylate, 2-acrylamido-2-methylpropanesulfonic acid, 3-acrylamido-3-methylbutanoic acid, sodium allylhydroxypropylsulfonate Cationic:
  N,N-dimethylaminoethyl methacrylate, N,N-dimethylpropyl(meth)acrylamide, (3-(meth)acrylamidopropyl)trimethylammonium chloride, diallyldimethylammonium chloride By way of non-limiting example, SACs made via copolymerization of ethylenically-unsaturated monomers include:

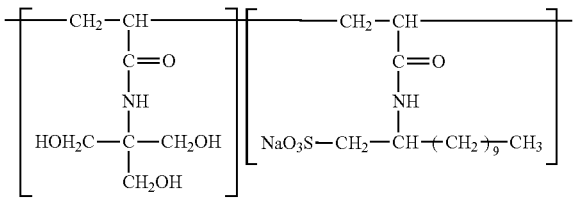

poly[tris(hydroxymethyl)acrylamidomethane-co-sodium 2-acrylamidododecylsulfonate]

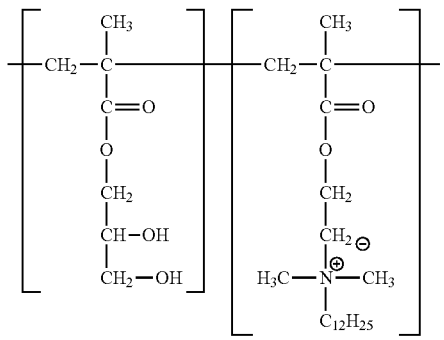

poly[glyceryl methacrylate-co-(2-methacryloyloxyethyl)dodecyldimethylammonium chloride]; and the like.

Additional synthetic routes for achieving the SACs of the present invention include via post-polymerization modification of precursor polymers comprising SRUs to render some repeat units amphiphilic. Nonlimiting examples include the reaction of superhydrophilic polymers comprised of repeat units comprising multiple hydroxyl functionalities, for example, starch, hydroxyethylcellulose, dextran, inulin, pullulan, poly(glyceryl methacrylate), poly[tris(hydroxymethyl)acrylamidomethane)], or poly(sucrose methacrylate), with reagents that will result in amphiphilic repeat units. Examples of suitable reaction schemes include:
  i) Esterification with alkenyl succinic anhydrides
  ii) Etherification with 1,2-epoxyalkanes
  iii) Etherification of with 3-chloro-2-hydroxypropylalkyldimethylammonium chlorides
  iv) Esterification with monoalkyl phosphate esters According to certain preferred embodiments, the SAC for use in the present invention is a polymer having multiple hydroxyl functionalities that is then post-polymerization modified to convert some of the repeat units to ARUs. In one particularly preferred embodiment, the polymer, e.g., a starch such as a starch dextrin polymer, that is esterified with an alkenyl succinic anhydride to convert some of the superhydrophilic anhydroglucose units to ARUs. The structure of one such suitable resulting SAC may be the C-6 sodium dextrin alkenylsuccinate, represented below:

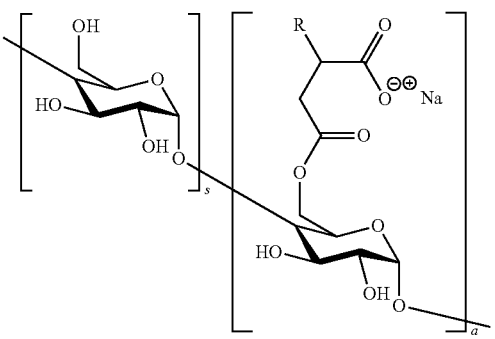

For example, the SAC may be a sodium dextrin dodecenylsuccinate, if $R=C_{12}H_{23}$. As will be recognized by one of skill in the art, such alkenyl succinate esters of polysaccharides may be synthesized as described, for example, in U.S. Pat. No. 2,661,349, incorporated herein by reference. Depending on the nature of the reaction conditions, molecular architecture, type of sugar repeat units, branch points and molecular weight, the modification of the sugar repeat units (AGU) may also occur at the C-2, C-3 or C-4 positions in addition to the C-6 position shown above.

The superhydrophilic amphiphilic copolymers derived from the reaction of the starting polysaccharide with the hydrophobic reagent comprises a polysaccharide bound with the hydrophobic reagent. In certain preferred embodiments, the SAC is a starch-based polysaccharide modified with one or more hydrophobic reagents. Examples of suitable starches include those derived from such plants as corn, wheat, rice, tapioca, potato, sago, and the like. Such starches can be of a native variety or those developed by plant breeding or by gene manipulation. In an embodiment of the invention, the starches include either the waxy versions of such starches (containing less than 5% amylose), high amylose starches (containing more than 40% amylose), those with a modified chain length (such as those disclosed in U.S. Pat. No. 5,9545,883, which is incorporated by reference in its entirety herein), and/or combinations thereof. In certain preferred embodiments, the starting starch is potato starch or tapioca starch. In certain other preferred embodiments, the starting starch is a waxy potato starch or waxy tapioca starch. In certain embodiments, the starch-based polysaccharide is modified by dissolving such low molecular weight starch or "dextrin" in water and reacting such starch with a hydrophobic reagent. The starch is desirably processed to lower its molecular weight by techniques known in the art, e.g., action of acid and heat, enzymatic, or thermal processing. The low molecular weight starch is dissolved in water, with optional heating, to form an aqueous solution and the pH of the aqueous solution is adjusted to about 2.0 by addition of an acid, such as a mineral acid (e.g. hydrochloric acid), to the solution. To minimize the removal of water at the end of the reaction, it is preferred that the starch solution be prepared at the highest solids possible. In an exemplary embodiment, a suitable working range for aqueous solids of the low molecular weight starch is from about 10% to about 80% starch based on the total weight of the solution. Preferably, the percent solids of the low molecular weight starch is from about 25% to about 75% based on total weight of solution. In another embodiment, the percent solids of the low molecular weight starch may be from about 35% to about 70% by weight of the total solution.

The viscosity of the aqueous solution of the polymeric surfactant is desirably low to minimize the detrimental effect of a high solids level of surfactant with pumping or flow of the solution. For this reason, in an embodiment of the invention, the Brookfield viscosity measured at room temperature (about 23° C.) at 200 rpm using spindle #3 for the polymeric surfactants of this invention may be less than about 1000 cps at 10% aqueous solids based on the total weight of the solution. In another embodiment, the Brookfield viscosity measured at room temperature (about 23° C.) at 200 rpm using spindle #3 of the 10% aqueous solution may be less than about 25 cps. In yet another embodiment, the Brookfield viscosity measured at room temperature (about 23° C.) at 200 rpm using spindle #3 of a 10% aqueous solution will be less than about 10 cps.

In a further step, the conversion of some of the superhydrophilic anhydroglucose units to ARUs is performed by reacting one or more hydrophobic reagents (e.g., alkenyl succinic anhydride) with the starch in the aqueous solution at a pH of about 8.5 at about 40° C. for about 21 hours to form an aqueous solution of SAC. Additional process steps such as cooling the aqueous solution of SAC to about 23° C. and neutralizing the solution to a pH of about 7.0 may then be performed. In an embodiment of the invention, the pH is adjusted by using a mineral acid, such as hydrochloric acid.

In certain preferred embodiments, the starch-based polysaccharide is modified with alkenyl succinic anhydride. Surprisingly, it has been found that a substituted succinic anhydride containing a C12 or longer side chain provides improved foam volume and foam stability than substituted succinic anhydrides having less than a C12 side chain. In certain preferred embodiments, the alkenyl succinic anhydrides is dodecenylsuccinic anhydride (DDSA). Exemplary treatment levels of the DDSA, on the dry basis of low molecular weight ranges from about 3 to about 25%. In another embodiment, the treatment level may be from about 5 to about 15% DDSA based on the dry weight of low molecular weight starting starch.

In an embodiment of the invention, the superhydrophilic amphiphilic copolymers derived from the reaction of the starting polysaccharide and DDSA, the bound DDSA on the starch-based polysaccharide may be of from about 3 about 15% based on the weight of dry starch. In another embodiment, the bound DDSA will be between 5 and 12% based on the dry weight of starch.

In an embodiment of the invention, the solution containing the low molecular weight polysaccharide may be then contacted with the DDSA using sufficient agitation to keep the DDSA uniformly dispersed throughout the solution. The reaction may then be run at temperatures between 25° C. and 60° C. while the pH of the reaction is kept from about 7.0 and about 9.0 by the slow and controlled addition of a suitable base. Some examples of such suitable base materials include, but not limited to, sodium hydroxide, potassium hydroxide, sodium, carbonate, potassium carbonate and calcium oxide (lime) and the like.

The solution of superhydrophilic amphiphilic copolymers of this invention is desirably clear or slightly hazy in order to provide acceptable aesthetics in personal care applications. A solution of 10% of the polymer is preferably less than about 400 ntu (as described in the experimental section below). In one embodiment, the clarity of a 10% aqueous solution of the polymeric surfactant is less than about 120 ntu. In another embodiment, the clarity is less than about 10 ntu.

In an exemplary embodiment of the invention, the hydrophobic reagent is a highly branched version of DDSA containing a 12 carbon side chain made from tetramerization of propene. It has been found that when the tetrapropene is then reacted with maleic anhydride in an ene-type reaction, it forms highly branched tetrapropenyl succinic anhydride (TPSA). Because this material is a slightly viscose oil and has acceptable water solubility (e.g., at about 2-5% in water at 23° C.), this reagent is capable of reacting favorably with the low molecular weight polysaccharide. In an embodiment of this invention, therefore, the hydrophobic reagent used to modify the low molecular weight starch may be TPSA.

In certain other preferred embodiments, the starch-based polysaccharide is modified with a long chain quaternary compound having at least one chain containing 3 or more carbon atoms. In another embodiment the long chain quaternary compound has at least one chain containing 6 or more and more preferably 12 or more carbon atoms, such as 3-chloro-2-hydroxypropyl-dimethyldodecylammonium chloride (sold commercially as QUAB(r) 342) or the epoxide form of such compound, 2,3 epoxypropyldimethyldodecylammonium chloride.

In still another embodiment of the invention, the one or more hydrophobic reagents may be a combination of reagents, such as, for example, a succinic anhydride and a long chain quaternary ammonium compound. A dialkylanhydride, such as stearyl anhydride, may also be suitable in the present invention.

In a further embodiment, the hydrophobic reagent has a molecular weight greater than about 220. Preferably, the hydrophobic reagent has a molecular weight greater than about 250.

In certain preferred embodiments, the modified starch-based polysaccharide has a weight average molecular weight of below 200,000. In certain preferred embodiments, the modified starch-based polysaccharide has a weight average molecular weight of from about 1,000 to 25,000 or 1,500 to 15,000 and more preferably about 3,000 to about 10,000.

In addition to starch-based polysaccharides, other polysaccharides are suitable for use in the present invention. Such polysaccharides may be derived from plant sources and those based on sugar-type repeat units. Some non-limiting examples of these polysaccharides are guar, xanthan, pectin, carrageenan, locust bean gum, and cellulose, including physical and chemically modified derivatives of the above. In embodiments of the invention, physical, chemical and enzymatic degradation of these materials may be necessary to reduce the molecular weight to the desired range to provide the viscosity for the desired application. Chemical modification can also be performed to provide additional functional properties (e.g., cationic, anionic or non-ionic) such as treatment with propylene oxide (PO), ethylene oxide (EO), alkyl chlorides (alkylation) and esterification such as 3-chloro-2-hydroxypropyl-trimethylammonium chloride, sodium tripolyphosphate, chloroacetic acid, epichlorohydrin, phosphorous oxychloride and the like.

Another non-limiting example of a SAC derived from post-polymerization modification of a polysaccharide includes:

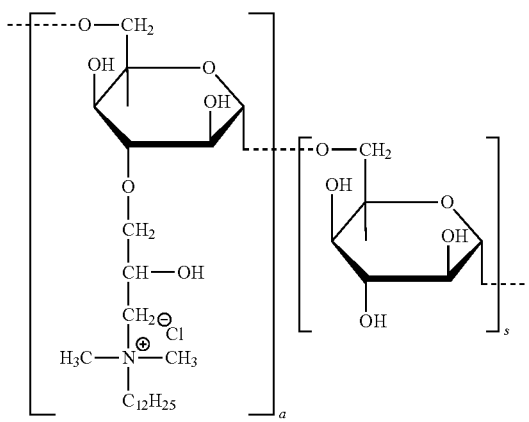

Dextran (poly[α(1→6)-D-glucose]) modified with 3-chloro-2-hydroxypropyllauryldimethylammonium chloride; and the like.

Other synthetic routes may include polymerization of amino acids and/or post-polymerization modification of polyaminoacids to achieve a SAC of the present invention, as well as, post-polymerization modification of hydrophilic polymers or amphiphilic polymers to achieve SACs of the present invention, and the like.

Applicants have discovered that the SACs of the present invention are useful in producing significant amounts of foam. For example, applicants have found certain polymers tested in accordance with the Polymer Foam Test of the present invention which have exhibited a Max Foam Volume of least about 200 mL. In certain preferred embodiments, the SACs of the present invention exhibit a Max Foam Volume of at least about 400 mL, more preferably at least about 500 mL, more preferably at least about 600 mL, and even more preferably at least about 700 mL.

Foam Stability is also important to the user of personal care products, such as described herein, as this often indicates a substantive, rich lather. Foam Stability of the SACs of this invention is measured as a percent of the foam decay of the Max Foam Volume after being undisturbed for 1000 seconds. Foam Stability is therefore calculated as the Foam Volume after 1000 seconds divided by the Max Foam Volume. Foam Stability that is about 15% or greater than the Max Foam Volume after 1000 seconds is considered within acceptable limits in accordance with the present invention. In an embodiment, the SACs of this invention have a foam stability of about 40% or greater than the Max Foam Volume after 1000 seconds. In another embodiment, the SACs provide foam stability of about 80% or greater than the Max Foam Volume after 1000 seconds. In yet another embodiment, the SACs provide foam stability about 90% or greater than the Max Foam Volume after 1000 seconds.

Applicants have discovered unexpectedly that according to embodiments of the invention, certain SACs not only provide foam that develops quickly and in high volume, but they are also useful in producing compositions having low irritation. According to certain preferred embodiments, applicants have discovered that SACs of the present invention may provide a PMOD % (measured in accord with the procedure described herein below and shown in the Examples) of less than about 90%, more preferably less than about 80%, more preferably less than about 50%, and more preferably less than about 40%, and are therefore useful in producing compositions having beneficially low irritation properties associated therewith.

As is described in U.S. Pat. No. 7,417,020, entitled, "COMPOSITIONS COMPRISING LOW-DP POLYMERIZED SURFACTANTS AND METHODS OF USE THEREOF," issued to Fevola et al., commonly assigned, and herein incorporated by reference in its entirety, PMOD % is calculated using the "average micelle hydrodynamic diameter $d_H$," a measure of average micelle size. The "fraction of micelles with $d_H$<9 nanometers (nm)" provides a measurement of the degree of irritation that may result from compositions that include surfactants. Surfactant micelles are rarely monodisperse in size and aggregation number (i.e., the average number of molecules of surfactant in a particular micelle). Instead, surfactant micelles tend to exist as a population with distributions of sizes and aggregation numbers that give rise to micelle size distribution functions. The "fraction of micelles with $d_H$<9 nanometers (nm)" is thus a measure of the capability of providing a distribution of micelles that, is "shifted" to favor larger micelles.

Any amounts of SACs suitable to produce micelle size distributions of the present invention may be combined according to the present methods. According to certain embodiments, the SAC is used in a concentration from greater than about 0.1% to about 30% by weight of active SAC in the composition. Preferably, the SAC is in a concentration from about 0.5 to about 20%, more preferably from about 1 to about 15%, even more preferably from about 2 to about 10% of active SAC in the composition. In certain other preferred embodiments, the compositions of the present invention comprise from about 0.5 to about 15%, more preferably from about 3 to about 15% or from about 1.5% to about 10% active SAC in the composition.

Applicants have discovered unexpectedly that by combining a superhydrophilic amphiphilic copolymer with a micellar thickener one can form a composition that has both low irritation and high amounts of flash foam thereby greatly enhancing the aesthetic appeal of the composition.

Applicants have noted a surprising ability of micellar thickeners to thicken a composition having a superhydrophilic amphiphilic copolymer and further allow the composition to quickly reduce viscosity upon dilution with water.

Without wishing to be bound by theory, upon investigation of Applicant's discovery, Applicants believe that the superhydrophilic amphiphilic copolymer is readily incorporated at the molecular level into the worm-like micelles whose formation is encouraged by the micellar thickener. The "intermolecular thickening network" thereby created is highly concentration sensitive, and thus, "breaks" readily upon dilution, allowing strong flash foam performance. This ability to disrupt the network upon dilution is particularly important for compositions which are reliant upon the superhydrophilic amphiphilic copolymer to generate foam, since superhydrophilic amphiphilic copolymers are larger and generally more slowly diffusing than conventional surfactants. This lack of mobility would otherwise reduce the ability of the superhydrophilic amphiphilic copolymer to generate flash foam.

As defined herein, the term, "micellar thickener," as will be readily understood by one skilled in the art, refers to a polymer that meets one or both of the two criteria described below. According to the first criteria, (I): the micellar thickener is a polymer that includes at least three hydrophilic repeat units or superhydrophilic repeat units, and further includes two or more independent hydrophobic moieties, and wherein the polymer has a relatively low weight-average molecular weight, e.g., less than about 100,000, preferably less than about 50,000, more preferably less than about 25,000, most preferably less than about 10,000. Preferred hydrophobic moieties include 10 or more carbon atoms, more preferably from 12 to 30 carbon atoms, even more preferably from 16 to 26 carbon atoms, and most preferably from 18 to 24 carbon atoms. Micellar thickeners that meet criteria (I) are generally believed to be suitable for modifying the corona (periphery) of surfactant micelles and, for convenience will hereinafter be referred to as "corona thickeners."

According to the second criteria, (II): the micellar thickener is a molecule that includes at least two non-ionic hydrophilic moieties; and includes either (a) two or more hydrophobic moieties that have a carbon chain that comprises 8 or more carbon atoms; or (b) one or more hydrophobic moieties that have a carbon chain that comprises 12 or more carbon atoms; and has a molecular weight less than about 5,000 (daltons), preferably less than about 3,000, more preferably less than about 2,000, most preferably less than about 1500. Micellar thickeners that meet criteria (II) are generally believed to be suitable for modifying the core (center) of surfactant micelles and, for convenience will hereinafter be referred to as "core thickeners."

Hydrophilic moieties, hydrophilic repeat units and superhydrophilic repeat units are defined above with respect to SACs. Preferred hydrophilic moieties include nonionics such as hydroxyl and ethyleneoxy. Preferred hydrophilic repeat units or superhydrophilic repeat units suitable for inclusion in the micellar thickener include ethyleneoxy, those repeat units derived from glycerol, glycidol, or glyceryl carbonate as well as those derived from hydrophilic and superhydrophilic ethylenically unsaturated monomers (e.g., acrylamide, N,N-dimethylacrylamide, acrylic acid, sodium acrylate, and sodium acryloyldimethyllaurate). Ethyleneoxy repeat units are particularly preferred. The number of hydrophilic repeat units may be from about 3 to about 1000, preferably from about 5 to about 500, more preferably from about 6 to about 400. Hydrophobic moieties are also defined above with respect to SACs. Preferred hydrophobic moieties suitable for inclusion are linear or branched, saturated or unsaturated alkyl or arylalkyl groups. In another preferred embodiment, the hydrophobic moiety includes adjoining repeat units or "blocks" of, for example, oxypropylene or (N-alkylacrylamide)s such as (N-t-butylacrylamide). For embodiments in which the hydrophobic moiety includes such blocks, the number of repeat units per block is preferably from about 3 to about 400, more preferably from about 5 to about 200. By "independent hydrophobic moieties" it is meant the hydrophobic moieties do not include any common atoms, i.e., they are positioned on different portions of the micellar thickener. In a preferred embodiment, the micellar thickener is non-ionic.

The micellar thickener may include one or more linking groups that serve, for example, to covalently bond a hydrophobic moiety to a hydrophilic repeat unit. Suitable linking groups include esters, thioesters, dithioesters, carbonates, thiocarbonates, trithiocarbonates, ethers, thioethers, amides, thioamides, carbamates/urethanes and xanthates. Preferred linking groups are esters and ethers.

In certain preferred embodiments, the micellar thickener is a corona thickener, as defined above. Preferably, the independent hydrophobic moieties of the corona thickener are terminal, i.e., the hydrophobic moieties are each positioned at a separate end or terminus of different branches of the polymer.

The corona thickener may be of varying chemical configurations. One suitable configuration is a linear configuration, such as one that may be defined by the structure below:

in which HRU is a hydrophobic repeat unit having h units of HRU per mole; L and L' are linking groups; and $R_1$ and $R_2$ are hydrophobic moieties. In certain preferred embodiments, the corona thickener is a linear molecule of the above formula in which h is 3-1000, preferably 5-500, more preferably 6-400, and more preferably 10-300.

A suitable example of a linear corona thickeners are a fatty acid diesters of polyethylene glycol (PEG), represented by the structure below:

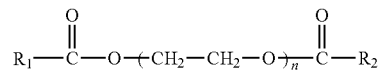

where L and L' are ester linking groups and the HRU is ethyleneoxy. One particular example of such a linear corona thickener in which $R_1$ and $R_2$ are $C_{17}H_{35}$ and n=150 repeat units is PEG-150 Distearate.

Other suitable examples of linear corona thickener are fatty acid esters of an ethoxylated fatty alcohol, represented by the structure below:

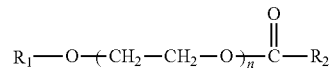

where L is an ether linking group and L' is an ester linking group and the HRU is ethyleneoxy. One particular example of such a linear corona thickener in which $R_1$ is $C_{24}H_{49}$ and $R_2$ is $C_{21}H_{43}$ and n=200 repeat units is Decyltetradeceth-200 Behenate.

Another suitable corona thickener having a linear configuration is one in which the hydrophilic repeat unit combines multiple hydrophilic functionalities, such as a hydrophobically modified ethoxylated urethane (HEUR). An example of such a corona thickener is shown below:

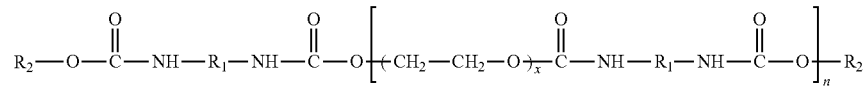

One particular example of such a HEUR in which $R_1$ is saturated diphenyl methylene, $R_2$ is $C_{18}H_{37}$, and x=150 repeat units is a PEG-150/Stearyl Alcohol/SMDI Copolymer.

Yet another suitable corona thickener having a linear configuration is one in which the hydrophobic moieties comprise three or more $C_3$ or greater alkoxy groups in sequence and the hydrophilic repeat unit repeat unit includes ethylene oxide, such as a PPO-PEO-PPO block copolymer. An example of such a corona thickener is shown below:

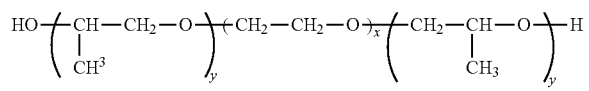

Other suitable configurations of the corona thickener are those that are branched or star-shaped in configuration. By "branched or star shaped" it is meant that the polymer includes multiple segments, e.g., 4 or 5 segments, such as those that extend from a common node structure. The node structure may be, but is not necessarily, a group of atoms that does not meet the above requirements for a hydrophobic moiety or a hydrophilic repeat unit. In one embodiment, the node structure is a branched hydrocarbon such as a neopentyl group (having 4 segments) shown below

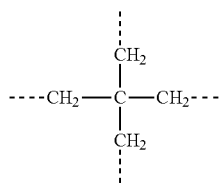

or a cyclic group such as a saccharide derived from fructose, glucose, galactose, mannose, glucosamine, mannuronic acid, guluronic acid onto which various functional groups have been reacted (an example of which, having 5 segments, is shown below).

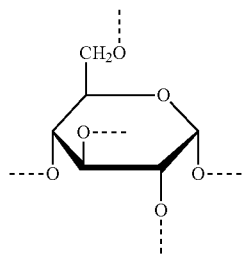

At least two of the segments that extend from the node structure include a terminal hydrophobic moiety, such as a terminal hydrophobic moiety that is joined to the node structure by an HRU. In certain embodiments, between 2 and 4 of the segments that are joined to the node structure include a terminal hydrophobic moiety, such as may be joined to the node structure by an HRU. In certain other embodiments one or more of the segments is a terminal HRU, e.g., one that is joined to the node structure, but does not form a bridge between the node structure and a terminal hydrophobic moiety.

Branched and star-shaped corona thickeners may include fatty acid polyesters of ethoxylated moieties. Suitable examples include fatty acid polyesters of ethoxylated polyglycerols. Other suitable examples include fatty acid polyesters of ethoxylated monosaccharides (e.g., fructose, glucose, galactose, mannose, glucosamine, mannuronic acid, guluronic acid). Fatty acid polyesters of ethoxylated glucosides are particularly preferred. One particular suitable example of a fatty acid polyester of an ethoxylated glucoside is a fatty acid diester of ethoxylated methyl glucoside, as represented by the structure below:

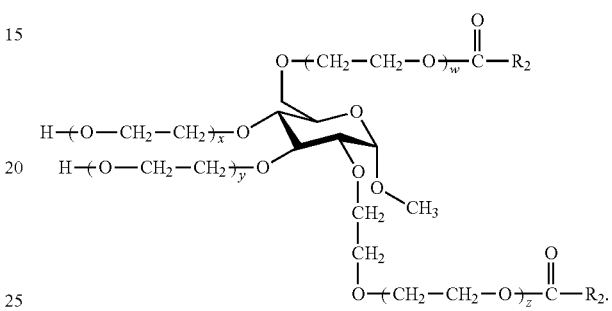

in which 4 distinct hydrophilic segments (here, each are comprised of ethyleneoxy HRUs) are linked via ether linkages to a methyl glucoside nodal structure. Two of the ethyleneoxy segments are also linked via an ester linking group to terminal fatty acid hydrophobic moieties. Thus, this particular corona thickener has 5 segments, two of these five include independent terminal hydrophobic moieties. Two of the remaining segments are terminal HRUs joined to the node structure via an ether linkage. One particular example of such a corona thickener is one in which the sum of the number of ethyleneoxy repeat units, w+x+y+z=119 and $R_1$ and $R_2$ are $C_{17}H_{33}$ (oleate), is PEG-120 Methyl Glucose Dioleate, sold commercially as Antil 120 Plus by Evonik. Other examples of suitable materials comprise ethoxylated methyl glucoside fatty acid esters of the structure below:

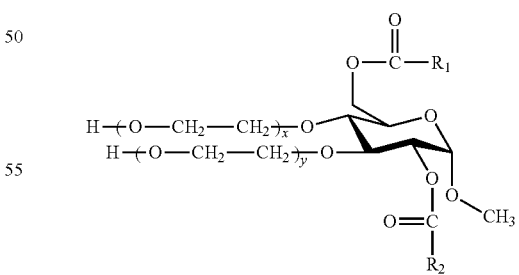

An example of such a material includes PEG-120 Methyl Glucose Dioleate, where x+y=120, $R_1$=$R_2$=$C_{17}H_{33}$, sold commercially as Glucamate DOE-120 by Lubrizol.

Another suitable fatty acid polyester of an ethoxylated glucoside is a fatty acid triester of ethoxylated methyl glucoside, as represented by the structure below:

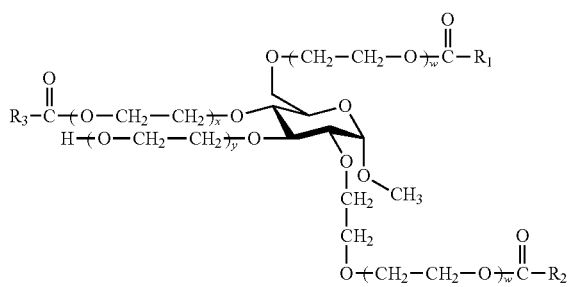

in which 4 distinct hydrophilic segments (here, each are comprised of HRUs) are linked via ether linkages to a methyl glucoside nodal structure. Three of the polyethyleneoxy segments are also linked via an ester linking group to terminal fatty acid hydrophobic moieties, and the fourth polyethyleneoxy segment terminates with a hydroxyl group. Thus, this particular corona thickener has 5 segments, three of these five include independent terminal hydrophobic moieties. One of the remaining segments is a terminal HRU joined to the node structure via an ether linkage. One particular example of such a corona thickener is one in which the sum of the number of ethyleneoxy repeat units, $w+x+y+z=119$ and $R_1$ and $R_2$ are $C_{17}H_{33}$ (oleate), is PEG-120 Methyl Glucose Trioleate. Other examples of suitable materials comprise fatty acid esters of ethoxylated methyl glucoside fatty acid esters of the formula below:

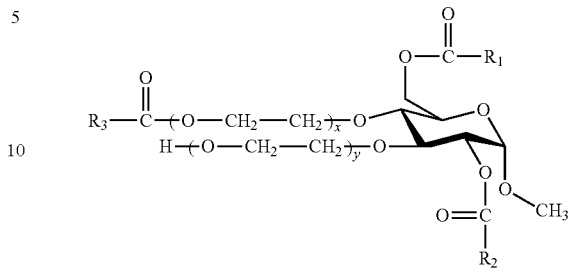

An example of such a material includes PEG-120 Methyl Glucose Trioleate, where $x+y=120$, $R_1=R_2=R_3=C_{17}H_{33}$, sold commercially as Glucamate LT by Lubrizol.

Another suitable example of corona thickener having a branched (or star-shaped) configuration is one having 4 segments. The 4 segments may each include an independent hydrophobic moiety. These may be joined to the node structure via HRUs. An example of a branched or star shaped corona thickener having 4 segments, a fatty acid polyester of a star shaped PEG, is represented by the structure below:

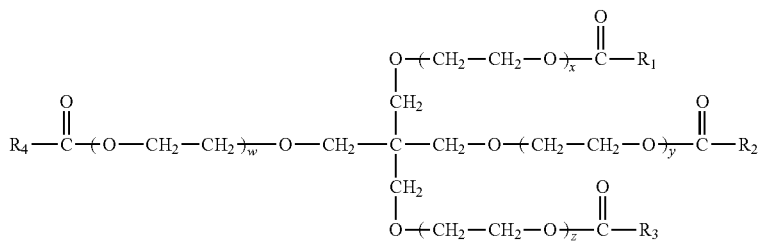

in which 4 distinct hydrophilic segments (here, each are comprised of ethyleneoxy repeat units) are linked via ether linkages to a nodal structure. The nodal structure consists of a pentaerythrityl functionality (i.e. a quaternary carbon atom having four pendant $CH_2$ groups bonded thereto). All four of the polyethyleneoxy segments are also linked via an ester linking group to terminal fatty acid hydrophobic moieties. One particular example of such a corona thickener is one in which the sum of the number of ethyleneoxy repeat units, $w+x+y+z=150$ and $R_1$, $R_2$, $R_3$, and $R_4$ are $C_{17}H_{35}$, is PEG-150 Pentaerythrytyl Tetrastearate.

Another suitable example of corona thickener having a star-shaped configuration is a PEO-PPO star block copolymer. A suitable structure is provided below:

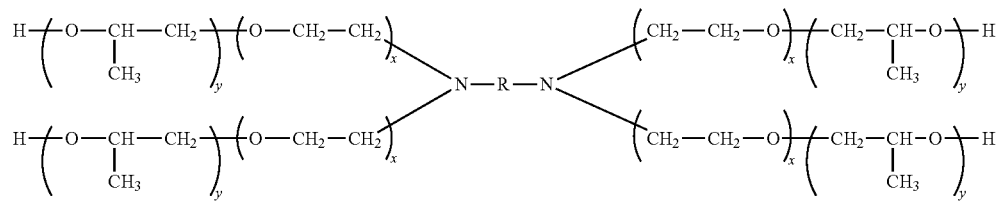

In the corona thickener shown above, N—R—N represents a nodal structure from which four segments emanate. R may be, for example an ethyl group, —CH$_2$CH$_2$—. Each branch includes an ethyleneoxy segment of x repeat units and terminates with a poly(oxypropylene) hydrophobic block.

In certain embodiments, the micellar thickener is a core thickener, as defined above. In certain preferred embodiments, core thickeners have a linear configuration. Examples of core thickeners include those derived from glycerol. One suitable example of a core thickener derived from glycerol is a glyceryl fatty acid ester, such as those defined by the structure below:

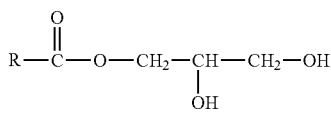

One particular example is glyceryl oleate, in which R=C$_{17}$H$_{33}$.

Another example of a branched core thickener derived from glycerol is a polyglycerol, such as polyglyceryl fatty acid esters, such as such as those defined by the structure below in which one of the hydrophilic moieties is positioned in an HRU:

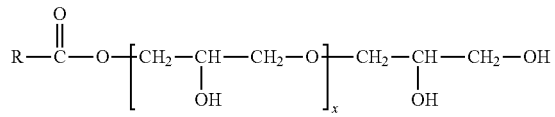

One particular example is polyglyceryl-10 oleate where R=C$_{17}$H$_{33}$ and x=9 (Polyaldo 10-1-O, available from Lonza Group LLC, Basel Switzerland).

Yet another example of suitable core thickeners include fatty acid mono and di-alkanolamides, such as those defined by the structure below:

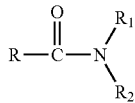

One particular example is Lauramide DEA, where R=C$_{11}$H$_{23}$ and R$_1$=R$_2$=CH$_2$CH$_2$OH.

Yet another example of suitable core thickeners include fatty acid esters of sorbitan, such as those defined by the structure below:

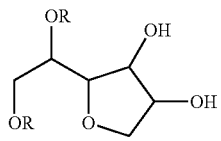

One particular example is sorbitan sesquicaprylate (available as Antil SC from Evonik Industries AG Dusseldorf, Germany), where R=C$_7$H$_{15}$CO or H with average 1.5 mol C$_7$H$_{15}$CO per mol sorbitan.

Any amounts of micellar thickeners suitable to increase viscosity of compositions of the present invention may be combined according to the present methods. For example, micellar thickener may be included in an amount in the formulation sufficient to increase the viscosity of the composition at least about 100 (when tested according to the Formulation Viscosity Test, described below), preferably sufficient to raise the viscosity at least about 200 cP, more preferably sufficient to raise the viscosity at least about 500 cP, even more preferably sufficient to raise the viscosity at least about at least about 1000 cP. The increases in viscosity specified above are as when compared with a composition which has water substituted for the micellar thickener.

According to certain embodiments, the micellar thickener is used in a concentration from greater than about 0.1% to about 15% by weight of active micellar thickener in the composition. Preferably, the micellar thickener is in a concentration from about 0.1 to about 10%, more preferably from about 0.1% to about 5%, even more preferably from about 0.2% to about 4%, even more preferably from about 0.5% to about 4%, and most preferably from about 1% to about 4% of active micellar thickener in the composition.

Applicants have discovered unexpectedly that the compositions of the present invention tend to have unexpected flash foaming properties. In particular, applicants have tested compositions of the present invention in accord with the Formulation Flash Foam Test described hereinbelow and have measured the foam volume at 20 cycles and the Foam Generation Rates associated therewith. Applicants have discovered that certain embodiments of the present invention produce a foam volume at 20 cycles of about 250 mL or greater. In certain more preferred embodiments, the embodiments exhibit a foam volume at 20 cycles of about 300 mL or greater, more preferably about 350 mL or greater, more preferably about 400 mL or greater, more preferably about 450 mL or greater, and more preferably about 500 mL or greater. Applicants have discovered that certain embodiments of the present invention exhibit a Foam Generation Rate of about 9 mL/cycle or greater. In certain more preferred embodiments, the embodiments exhibit a Foam Generation Rate of about 10 mL/cycle or greater, more preferably about 12 mL/cycle or greater, more preferably about 14 mL/cycle or greater, more preferably about 16 mL/cycle or greater, more preferably about 18 mL/cycle or greater, more preferably about 20 mL/cycle or greater, and more preferably about 22 mL/cycle or greater.

Compositions useful in the present invention may also include any of a variety of conventional polymerized surfactants that do not meet the requirements specified above in order to be specified as a SAC. Examples of suitable conventional polymerized surfactants include those described in U.S. Pat. No. 7,417,020, entitled, "COMPOSITIONS COMPRISING LOW-DP POLYMERIZED SURFACTANTS AND METHODS OF USE THEREOF," issued to Fevola et al.

Compositions useful in the present invention may also include any of a variety of monomeric surfactants. By "monomeric surfactants" it is meant any surface active agents that do not meet the definition of "polymerized surfactant" as defined above. The monomeric surfactants may be anionic, nonionic, amphoteric or cationic, examples of which are detailed below.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

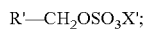

alkyl ether sulfates of the formula

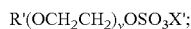

alkyl monoglyceryl ether sulfates of the formula

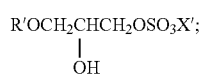

alkyl monoglyceride sulfates of the formula

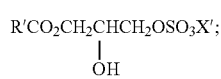

alkyl monoglyceride sulfonates of the formula

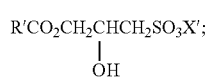

alkyl sulfonates of the formula

alkylaryl sulfonates of the formula

alkyl sulfosuccinates of the formula:

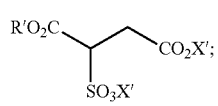

alkyl ether sulfosuccinates of the formula:

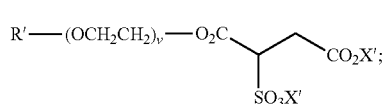

alkyl sulfosuccinamates of the formula:

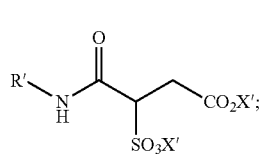

alkyl amidosulfosuccinates of the formula

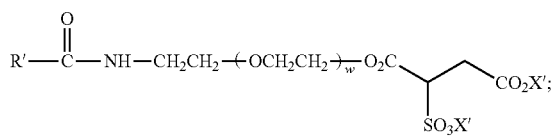

alkyl carboxylates of the formula:

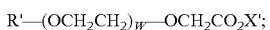

alkyl amidoethercarboxylates of the formula:

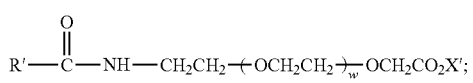

alkyl succinates of the formula:

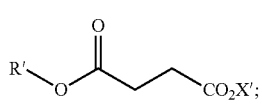

fatty acyl sarcosinates of the formula:

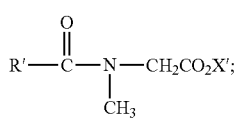

fatty acyl amino acids of the formula:

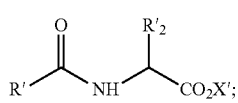

fatty acyl taurates of the formula:

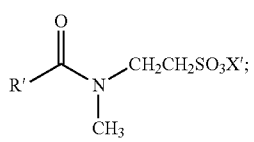

fatty alkyl sulfoacetates of the formula:

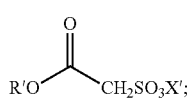

alkyl phosphates of the formula:

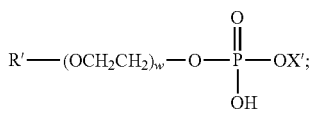

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic l-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Croda, Inc. of Edison, N.J. under the tradename, "Atlas G-4280." Polysorbate 20, which is the laurate monoester of a mixture of sorbitol and sorbitol anhydrides condensed with approximately 20 moles of ethylene oxide, is available commercially from Croda, Inc. of Edison, N.J. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the tradename, "Plantaren 2000."

Any of a variety of amphoteric surfactants are suitable for use in the present invention. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di); N-alkyl β-aminoproprionic acids; alkylpolyamino carboxylates; and mixtures thereof.

Examples of suitable amphocarboxylate compounds include those of the formula:

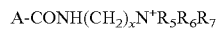

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

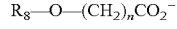

wherein
$R_8$ is an alkylene group having from about 2 to about 3 carbon atoms and n is 1 or 2; and
$R_7$ is a carboxyalkyl group containing from about 2 to about 3 carbon atoms;
Examples of suitable alkyl betaines include those compounds of the formula

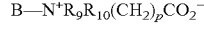

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.
A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

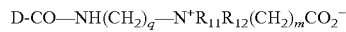

wherein
D is an alkyl or alkenyl group having from about 7 to about 21, e.g. from about 7 to about 15 carbon atoms;
$R_{11}$ and $R_{12}$ are each independently an alkyl or Hydroxyalkyl group having from about 1 to about 4 carbon atoms;
q is an integer from about 2 to about 6; and m is 1 or 2.

One amidoalkyl betaine is cocamidopropyl betaine, available commercially from Evonik Industries of Hopewell, Va. under the tradename, "Tegobetaine L7."

Examples of suitable amidoalkyl sultaines include those compounds of the formula

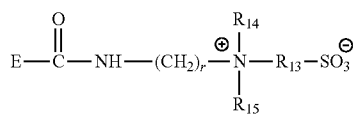

wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;
r is an integer from about 2 to about 6; and
$R_{13}$ is an alkylene or hydroxyalkylene group having from about 2 to about 3 carbon atoms;

In one embodiment, the amidoalkyl sultaine is cocamidopropyl hydroxysultaine, available commercially from Rhodia Novecare of Cranbury, N.J. under the tradename, "Mirataine CBS."

Examples of suitable amphophosphate compounds include those of the formula:

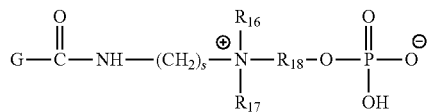

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

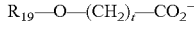

wherein
$R_{19}$ is an alkylene or hydroxyalkylene group having from about 2 to about 3 carbon atoms and
t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Croda, Inc. of Edison, N.J. under the tradename, "Monateric 1023," and those disclosed in U.S. Pat. No. 4,380,637, which is incorporated herein by reference.

Examples of suitable phosphobetaines include those compounds of the formula:

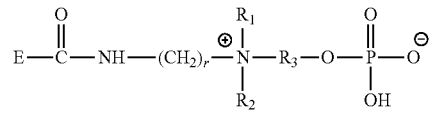

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

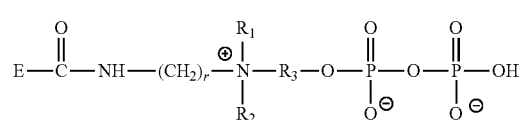

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

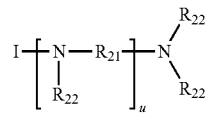

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any amounts of monomeric surfactant suitable to produce low small micelle fraction composition may be combined according to the present methods. For example, the amount of monomeric surfactants used in the present invention may be from about 0.1 to about 30%, more preferably from about 0.5 to about 20%, even more preferably from about 1 to about 15% of total active monomeric surfactant in the composition, and even more preferably from about 2% to about 10%.

Any relative amounts of polymerized surfactants and monomeric surfactant suitable to produce low small micelle fraction composition may be combined according to the present methods. According to certain embodiments, the compositions comprise a ratio of SAC to the sum total of all monomeric surfactants of from about 0.1:1 to about 5:1, and preferably from about 0.25:1 to about 3:1.

The compositions of the present invention may comprise any of a variety of additional other ingredients used conventionally in healthcare/personal care compositions ("personal care components"). These other ingredients nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

The pearlescent or opacifying agent may be introduced to the mild cleansing composition as a pre-formed, stabilized aqueous dispersion, such as that commercially available from Cognis Corporation of Ambler, Pa. under the tradename, "Euperlan PK-3000." This material is a combination of glycol distearate (the diester of ethylene glycol and stearic acid), Laureth-4 ($CH_3(CH_2)_{10}CH_2(OCH_2CH_2)_4OH$) and cocamidopropyl betaine and may be in a weight percent ratio of from about 25 to about 30:about 3 to about 15:about 20 to about 25, respectively.

Compositions useful in the present invention may also include any of a variety of conventional thickeners that do not meet the requirements specified above in order to be considered micellar thickeners. Examples of suitable conventional thickeners include various thickeners having molecular weights of greater than about 100,000 grams per mole, including chemistries such as: hydroxyalkyl cellulose; alkyl cellulose; hydroxyalkyl alkyl cellulose; xanthan and guar gums, succinoglycan gums; and mixtures thereof.

Examples of suitable thickening agents nonexclusively include: mono or diesters of 1) polyethylene glycol of formula: $HO-(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); hydrophobically-modified ethoxylated urethanes (HEURs); xanthan and guar gums; and mixtures thereof. Preferred thickeners include polyethylene glycol ester, and more preferably PEG-150 distearate which is available from the Hallstar Company of Chicago, Ill. under the tradename, "PEG 6000 DS".

Any of a variety of commercially available secondary conditioners, such as volatile silicones, which impart additional attributes, such as gloss to the hair are suitable for use in this invention. The volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable secondary conditioners include cationic polymers, including polyquarterniums, cationic guar, and the like.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, polyglycerols, and mixtures thereof; 2) polyalkylene glycol of the formula: $HO-(R''O)_b-H$, wherein R'' is an alkylene group having from about 2 to about 3 carbon atoms and b is an integer of from about 2 to about 10; 3) polyethylene glycol ether of methyl glucose of formula $CH_3-C_6H_{10}O_5-(OCH_2CH_2)_c-OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include, for example, parabens, quaternary ammonium species, phenoxyethanol, benzoates, DMDM hydantoin, and are present in the composition in an amount, based upon the total weight of the composition, from about 0 to about 1 percent or from about 0.05 percent to about 0.5 percent.

The SAC, optional micellar thickener, and optional monomeric surfactants and optional other components of the composition may be combined according to the present invention via any conventional methods of combining two or more fluids or solids. For example, one or more compositions comprising, consisting essentially of, or consisting of at least one SAC and one or more compositions comprising, consisting essentially of, or consisting of water, monomeric surfactants or suitable ingredients may be combined by pouring, mixing, adding dropwise, pipetting, pumping, and the like, one of the compositions comprising the polymerized surfactant into or with the other in any order using any conventional equipment such as a mechanically stirred propeller, paddle, and the like.

The methods of the present invention may further comprise any of a variety of steps for mixing or introducing one or more of the optional components described hereinabove with or into a composition comprising a SAC either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising the polymerized surfactant.

The pH of the present compositions is not critical, but may be in a range that does not facilitate irritation to the skin, such as from about 4 to about 7. The viscosity of the personal care composition is not critical, although it may be a spreadable cream or lotion or gel. In certain embodiments, the personal care composition has a viscosity from about 200 cP to about 10,000 cP, such as when evaluated according to the Formulation Viscosity Test, as described below.

The compositions may be made into a wide variety of product types that include but are not limited to cleansing liquid washes, gels, sticks, sprays, solid bars, shampoos, pastes, foams, powders, mousses, shaving creams, wipes, patches, nail lacquers, wound dressing and adhesive bandages, hydrogels, films and make-up such as foundations, mascaras, and lipsticks. These product types may comprise several types of carriers including, but not limited to solutions, emulsions (e.g., microemulsions and nanoemulsions), gels, and solids. Other carriers include solvents, which can include, but are not limited to water, acetone, alcohols, such as isopropanol and ethanol, ethylene glycol, glycerin, dimethylformamide, tetrahydrofuran, dimethylsulfoxide, sorbitol and ethers and ester of sorbitol. In an embodiment of the invention, water and alcohols are the preferred carriers. Other carriers can be formulated by those of ordinary skill in the art.

The compositions useful in the present invention may include formulations suitable for administering to the target tissues, such as human skin. In one embodiment, the composition comprises a superhydrophilic amphiphilic copolymer and a carrier, preferably a cosmetically-acceptable carrier. As used herein, the term "cosmetically-acceptable carrier" means a carrier that is suitable for use in contact with the skin without undue toxicity, incompatibility, instability, irritation, allergic response, and the like. The compositions can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof. In certain preferred embodiments, the compositions of the present invention are aqueous solutions comprising from about 50% to about 99% by weight of water.

According to certain embodiments, compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32 43 (1972) and the International Cosmetic Ingredient Dictionary and Handbook, eds. Wenninger and McEwen, pp. 1656 61, 1626, and 1654 55 (The Cosmetic, Toiletry, and Fragrance Assoc., Washington, D.C., 7.sup.th Edition, 1997) (hereinafter "ICI Handbook") contains numerous examples of suitable materials. A lotion can be made from such a solution. Lotions typically comprise from about 1% to about 20% (e.g., from about 5% to about 10%) of an emollient(s) and from about 50% to about 90% (e.g., from about 60% to about 80%) of water.

The present compositions may be of varying phase compositions, but are preferably aqueous solutions or otherwise include an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

In certain embodiments, the compositions produced via the present invention are preferably used as or in personal care products for treating or cleansing at least a portion of a human body. Examples of certain preferred personal care products include various products suitable for application to the skin, hair, oral and/or perineal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as flash foaming characteristics, rheology, and functionality, even at high surfactant concentrations. Such products may further include a substrate onto which a composition is applied for use on the body. Examples of suitable substrates include a wipe, pouf, sponge, and the like as well as absorbent articles, such as a bandage, sanitary napkin, tampon, and the like.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. Any of a variety of actives or benefit agents known in the art for treating such conditions may be used in the present invention.

What is meant by a "benefit agent" is an element, an ion, a compound (e.g., a synthetic compound or a compound isolated from a natural source) or other chemical moiety in solid (e.g. particulate), liquid, or gaseous state and compound that has a cosmetic or therapeutic effect on the skin.

The compositions of the present invention may further include one or more benefit agents or pharmaceutically-acceptable salts and/or esters thereof, the benefit agents generally capable of interacting with the skin to provide a benefit thereto. As used herein, the term "benefit agent" includes any active ingredient that is to be delivered into and/or onto the skin at a desired location, such as a cosmetic or pharmaceutical.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits to the skin, such as, but not limited to, depigmentation agents; reflectants; amino acids and their derivatives; antimicrobial agents; allergy inhibitors; anti-acne agents; anti-aging agents; anti-wrinkling agents, anti-septics; analgesics; shine-control agents; antipruritics; local anesthetics; anti-hair loss agents; hair growth promoting agents; hair growth inhibitor agents, antihistamines; antiinfectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavonoids; sensates; anti-oxidants; hair lighteners; sunscreens; anti-edema agents, neo-collagen enhancers, film-forming polymers, chelating agents; anti-dandruff/seb-horreic dermatitis/psoriasis agents; keratolytics; and mixtures thereof.

The cleansing methods of the present invention may further comprise any of a variety of additional, optional steps associated conventionally with cleansing hair and skin including, for example, lathering, rinsing steps, and the like.

As noted above, the SACs of the present invention are particularly advantageous in healthcare applications. However, the SACs also have application in non-healthcare applications, for example in industrial uses. Non-limiting examples of such applications include detergent applications, anti-scale applications, such as autodish, emulsification of oils and tars, foam boosting for reducing the density and aerating porous materials, cleansing of fabrics or industrial surfaces, as a surface tension modifier for coating applications, providing foaming and/or cleaning for applications that require biodegradable components, and the like.

In embodiments of the invention comprising compositions that include the SACs of this invention, the compositions may include functional materials to enhance performance in each particular application. Some examples of these functional materials are: surfactants, anti-scale polymers, chelating agents, viscosity modifiers, antioxidants, colloidal stabilizers and anti-re-deposition polymers. The SACs of this invention can also be used to reduce the density of and provide porosity within a solid article, in which in these applications the SAC will be used in conjunction with a structural material. Such structural materials can include activated charcoal, absorbent materials, such as polyacrylic acid, structural materials such as cellulose, polyvinyl alcohol, polystyrene and polyacrylates and copolymers of these. The above list illustrates the broad uses of a foam stabilizing SAC and is not meant to limit the scope of this invention.

EXAMPLES

The following Drop Shape Analysis ("DSA"), Dynamic Light Scattering ("DLS"), Polymer Foam, Formulation Foam, Solution Viscosity, Formulation Flash Foam, and Formulation Viscosity tests are used in the instant methods and in the following Examples. In particular, as described above, the DSA test is used to determine the degree to which a polymeric material (e.g. a SAC) in a composition reduces surface tension, according to the present invention; the DLS test, Polymer Foam Test, and Solution Viscosity may be used to determine the suitability of a particular SAC to provide reduced irritation and high foam; and the Formulation Flash Foam Test and Formulation Viscosity tests may be used to determine degree to which a particular composition can generate high foam, and/or provide beneficial viscosity, which is often desirable for cleansing compositions.

Unless otherwise indicated, the amounts of ingredients in the Example and Comparative compositions listed in the tables are expressed in w/w % of ingredient based on the total composition.

Drop Shape Analysis Test ("DSA Test")

Dynamic surface tension reduction is determined via the DSA Test. Drop Shape Analysis (DSA, also known as Pendant prop Method or PDM) is a well-known method for measuring the static interfacial or surface tension ($\gamma$) as a function of time. The surface tension measured by DSA is determined by fitting the shape of the hanging drop (captured in a video image) to the Young-Laplace equation, which relates inter-facial tension to drop shape. The Laplace equation is the mechanical equilibrium condition for two homogeneous fluids separated by an interface (*Handbook of Applied Surface and Colloid Chemistry*, Vol. 2; Holmberg, K., Ed.; John Wiley & Sons: Chicester, U.K., 2002, pp 222-223). It relates the pressure difference across a curved interface to the surface tension and the curvature of the interface:

$$\gamma\left(\frac{1}{R_1} + \frac{1}{R_2}\right) = \Delta P \qquad (1)$$

where $R_1$ and $R_2$ are the two principal radii of curvature, and $\Delta P$ is the pressure difference across the interface. In the absence of any external forces other than gravity (g), $\Delta P$ may be expressed as a linear function of the elevation:

$$\Delta P = \Delta P_0 + (\Delta \rho)gz \qquad (2)$$

where $\Delta P_0$ is the pressure difference at a reference plane and z is the vertical coordinate of the drop measured from the reference plane. Thus for a given value of $\gamma$, the shape of a drop may be determined (refer to Lahooti S., del Río O. I., Cheng P., Neumann A. W. In *Axisymmetric Drop Shape Analysis (ADSA)*, Neumann A. W., Spelt J. K., Eds. New York: Marcel Dekker Inc., 1996, Ch. 10; Hoorfar M., Neumann, A. W. Adv. Coll. and Interface Sci., 2006, 121 (1-3), 25-49).

Solutions for the determination of surface tension were prepared as follows: a polymer sample (1150 mg active solids) is diluted in Millipore-Q deionized water (200 mL) in an acid-washed glass flask with glass stopper. This stock solution is mixed by manually shaking for five minutes and allowed to stand overnight. A dilution (¼) of the stock solution is prepared by further diluting the stock solution with Millipore-Q water in acid-washed glassware—this is the sample is used for DSA analysis.

The samples are analyzed using a DSA 100 instrument (Krüss GmbH, Hamburg, Germany) operating at 25.0° C. The drop was monitored over 120 seconds and images were captured approximately every 0.16 seconds for the first 10 seconds, every 0.5 seconds for the next 50 seconds, and every second for the last 60 seconds. All of the captured images are analyzed to determine the surface tension at each time frame. Surface tension values are calculated using the prop Shape Analysis (DSA) for Windows™ package (Krüss GmbH, Hamburg, Germany). Dynamic reduction of surface tension is reported as the time in seconds required to reduce the surface tension of the test solution to 55 mN/m, $t_{\gamma=55}$. The reported values of $t_{\gamma=55}$ are the average of three individual measurement runs.

Solution Viscosity Test:

Solution viscosities of solutions of test material (e.g., SACs), 2 wt % in DI water were conducted on a controlled-stress rheometer (AR-2000, TA Instruments Ltd., New Castle, Del., USA). Steady-state shear stress sweeps were performed at 25.0±0.1° C. using a double-wall Couette geometry. Data acquisition and analysis were performed with the Rheology Advantage software v4.1.10 (TA Instruments Ltd., New Castle, Del., USA). Zero-shear apparent viscosities for Newtonian fluids are reported as the average of viscosity values obtained over a range of shear stresses (0.02-1.0 Pa). For pseudoplastic (shear-thinning) fluids, zero-shear apparent viscosities were calculated via the fitting of shear stress sweep data to an Ellis viscosity model.

Polymer Foam Test:

The following Polymer Foam Test was performed on various test materials (e.g., polymerized surfactant) to determine the foam volume upon agitation according to the present invention. The Polymer Foam Test is conducted as follows: a solution of the test material (1000 mL of a 0.5 wt % solution) is first prepared according to the following procedure: 900 g deionized (DI) water is charged to an appropriately sized glass beaker equipped with a mechanical stirrer and hotplate. While mixing at low to medium speeds and heating to 75-80° C., the polymer sample (5.0 g active solids) is slowly added to the beaker. The polymer solution is allowed to mix at 75-80° C. for 15 min, or until the polymer is completely dissolved, at which point heating is ceased and the solution allowed to begin cooling to ambient temperature. When the batch temperature falls below 40° C., DMDM Hydantoin (3.0 g of a 55 wt % solution, sold as Glydant from Lonza) and Tetrasodium EDTA (5.0 g of a 50 wt % solution, sold as Versene XL from Dow Chemical) are added to the solution. The solution pH is adjusted to pH=7.0±0.2 using 20 wt % Sodium Hydroxide solution and/or 20 wt % Citric Acid solution, followed by the addition of DI water in q.s. to 100 wt %. The polymer solution is allowed to cool to ambient temperature and stored in a sealed glass jar until ready for use. To determine the Maximum Foam Volume, the polymer solution (1000 mL) was added to the sample tank of a Sita R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam Volume data was collected at the end of each stir cycle and the average and standard deviation of the three runs was determined. The Maximum Foam Volume was reported for each Example as the value after the thirteenth stir cycle.

Formulation Foam Test:

The following Formulation Foam Test was performed on various personal care compositions to determine the foam volume upon agitation according to the present invention. First, a solution of the test composition is prepared in simulated tap water. To represent the hardness of tap water, 0.36 g of calcium chloride is dissolved in 995 g of DI water. Five (5.0) grams of test composition is then added to this solution and mixed until homogeneous. To determine the Formulation Foam Volume, the composition (1000 mL) was added to the sample tank of a Sita R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviation of the three runs was determined. The Formulation Foam was reported for each Example as the value after the thirteenth stir cycle.

Dynamic Light Scattering Test ("DLS Test"):

Dynamic light scattering (DLS, also known as Photon Correlation Spectroscopy or PCS) is a well-known method for determination of average micelle size (measured as hydrodynamic diameter, $d_H$) and micelle size distribution (A comprehensive explanation of the technique can be found in the ISO test method ISO013321:1996(E). The hydrodynamic size measured by DLS is defined as the size of a hypothetical hard sphere that diffuses in the same fashion as that of the particle being measured. In practice, micellar species are dynamic (tumbling), solvated species that may be isotropic (spherical) or anisotropic (e.g. ellipsoidal or cylindrical) in shape. Because of this, the diameter calculated from the diffusion properties of the micelle will be indicative of the apparent size of the dynamic hydrated/solvated particle; hence the terminology, "hydrodynamic diameter." Micellar solutions for determination of micelle $d_H$ are prepared by diluting the compositions to 3.0% of their original concentration with 0.1 μm-filtered deionized water, obtained from a Millipore-Q filtration system. (The target dilution of 3.0% is chosen because it is within the typical concentration range of 1.0%-10% dilution that is encountered during the use of rinse-off personal care compositions. The target dilution is also within the range of dilutions employed in the TEP test.) The samples are agitated on a vortex mixer at 1000 rpm for a minimum of five minutes and then allowed to stand overnight prior to analysis. Samples are passed through a 0.2 μm Ana top-Plus syringe filter into dust-free disposable acrylic sizing cuvettes and sealed.

The samples are analyzed using a Zetasizer Nano ZS DLS instrument (Malvern Instruments, Inc., Southborough, Mass.) operating at 25.0° C. Samples must yield a minimum count rate of 100,000 counts per second (cps) for accurate determination of micelle $d_H$ and micelle size distribution. For samples with count rates below this minimum, the sample concentration may be gradually increased (i.e. diluted less) until the minimum count rate is achieved, or in some cases, the sample may be run in neat form. Values of micelle $d_H$ and the micelle size distribution are calculated using the Dispersion Technology Software (DTS) v4.10 package (Malvern Instruments Inc., Southborough, Mass.), which calculates the Z-average micelle $d_H$ according to the ISO13321 test method. Values of average micelle $d_H$ are reported herein as the Z-average micelle $d_H$. The reported values of micelle $d_H$ are the average of three individual measurement runs. The intensity distribution of micelle size calculated by the DTS software is used to calculate the fraction of micelles having values of $d_H$ under a given size limit.

Additives exhibiting relatively large values of $d_H$ (i.e. greater than about 200 nm) compared to micellar species, for example, high MW polymeric rheology modifiers, polymeric conditioners, particulate opacifiers, (micro)emulsions of hydrophobic emollients, silicone (micro)emulsions, etc., are routinely added to personal care compositions comprising micellar species. To those skilled in the art of DLS, it is apparent that such nonmicellar materials will exhibit light scattering intensities orders of magnitude greater than the relatively smaller micellar species in the diluted sample. The scattering intensity of such materials will overwhelm the scattering signal of the micellar species, thus interfering in the accurate determination of micelle $d_H$. Typically, this type of interference will lead to an erroneously large measured value of micelle $d_H$. To avoid such interference, it is most preferable to measure the micelle $d_H$ of the composition in the absence of additives exhibiting values of $d_H$ greater than about 200 nm. Those skilled in the art of DLS will recognize that additives exhibiting large values of $d_H$ should be separated from the sample via filtration or ultracentrifugation prior to determination of the micelle $d_H$ of the sample. Alternatively, higher order analysis of the DLS data using the Dispersion Technology Software v4.10 package may also be employed to obtain enhanced resolution and properly characterize micelle $d_H$ in the presence of nonmicellar scattering species.

In accord with the above description and as shown hereafter in the Examples, the "PMOD %" and "PMODz-average" associated with a test material (e.g., polymerized surfactant) are calculated by preparing a model composition comprising about 4.8 active weight % of the test material, 0.3 weight percent of a combination of sodium methyl- (and) sodium propyl- (and) sodium ethyl paraben, (such as the product commercially available as Nipasept Sodium), 0.25 weight percent of tetrasodium EDTA (such as Versene 100 XL), with q.s. water, and using the DLS test to measure the fraction of micelles having a dH of less than 9 nm in the resulting model composition (PMOD %), and the z-average micelle dH associated therewith (PMODz-average). Applicants have recognized that in certain embodiments, the test material may be incompatible with the above model composition. Thus, if, and only if, the formulation of the above model composition results in two separate liquid phases and/or precipitation of the polymer surfactant, then the PMOD % and PMODz-average procedure comprises making a composition comprising about 4.8 active weight % of the test material, 0.5 weight percent of sodium benzoate, 0.25 weight percent of tetrasodium EDTA (such as Versene 100 XL), with q.s. citric acid to a pH of 4.8±0.2, with q.s. water, and using the DLS test to measure the fraction of micelles having a $d_H$ of less than 9 nm in the resulting model composition (PMOD %), and the z-average micelle $d_H$ associated therewith (PMODz-average).

Formulation Viscosity Test:

The following Viscosity Test was performed on various personal care compositions to determine the viscosity according to the present invention. Viscosities of test formulations were conducted at 25° C. using a Brookfield DV-I+ viscometer (Brookfield Engineering Laboratories, Inc. Middleboro, Mass.). Measurement parameters are selected so as to ensure "% torque" is between 40%-60% on the viscometer. Typical operating parameters are spindle #S62 operating at six rpm. One skilled in the art will recognize that in order to accommodate samples of higher viscosities, it may be necessary to change spindle selection or operating speed to enable a viscosity measurement.

Formulation Flash Foam Test:

The following Formulation Flash Foam Test was performed on various personal care compositions to determine the foam volume as a function of agitation, according to the present invention. To a bottom of a clean, dry 500 mL Pyrex glass graduated mixing cylinder was charged 50 g of test formulation. Deionized water (50 g) was then slowly and carefully poured down the side of the flask, with care taken to avoid mixing with the test formulation, so as to form a separate layer of water on top of the test formulation. The cylinder was fitted with a stopper secured with Parafilm and mounted in the Vertical Rotator Assembly of a Gaum Foam Machine (Gaum Inc., Robbinsville, N.J.). The cylinder was rotated at cycle speed #30 for a total of 20 cycles. The foam volume was recorded at two cycle intervals by stopping rotation and reading the foam volume on the graduated cylinder. The height of the foam was measured at the level where the foam bubbles are dense enough to render the graduated cylinder opaque. The Formulation Flash Foam Value was reported as the average of two individual runs. The Foam Generation Rate, FGR, was calculated by plotting Formulation Flash Foam Value as a function of shake cycle (2 cycles to 20 cycles) and fitting the data to a straight line function. The FGR is the slope of the resulting linear fit.

Examples E1-E6 and Comparative Examples C1-C3

Preparation of Polymerized Surfactants

The following polymerized surfactants, Inventive Examples E1-E6 and Comparative Examples C1-3 were prepared.

TABLE 1

| Example | Description | total #RU ("DP") | mol % ARU | avg # ARU (a) | avg # SRU (s) |
|---------|-------------|------------------|-----------|---------------|---------------|
| C1 | hydrolyzed PA-18 (Octadecene/MA Copolymer) | 50 | 100 | 50 | 0 |
| C2 | hydrolyzed PA-14 (Tetradecene/MA Copolymer) | 50 | 100 | 50 | 0 |
| C3 | Natrosol Plus CS 330 (Cetyl Hydroxyethylcellulose) | 1204 | 1.0 | 12.0 | 1192 |
| E1 | Sodium Tapioca Dextrin Dodecenylsuccinate | 39 | 7.7 | 3.0 | 36 |
| E2 | Sodium Tapioca Dextrin Dodecenylsuccinate | 35 | 6.3 | 2.2 | 33 |
| E3 | Sodium Tapioca Dextrin Dodecenylsuccinate | 37 | 5.8 | 2.1 | 35 |
| E4 | Sodium Potato Dextrin Dodecenylsuccinate | 43 | 3.3 | 1.4 | 42 |
| E5 | Sodium Potato Dextrin Dodecenylsuccinate | 33 | 3.0 | 1.0 | 32 |
| E6 | Sodium Potato Dextrin Dodecenylsuccinate | 33 | 5.0 | 1.7 | 31 |

The polymerized surfactants noted in Table 1 were prepared as follows: PA-18, hydrolyzed, of Comparative Example C1 was obtained by performing a reaction of a 1:1 alternating copolymer of 1-octadecene and maleic anhydride (PA-18 Low Viscosity Low Color grade, commercially available from Chevron Phillips Chemical, LLC) with sodium hydroxide in aqueous solution to yield a octadecene/MA copolymer having an average of about 50 amphiphilic repeat units on a weight average basis, a mole fraction of amphiphilic repeat units of about 100%, and a hydrophobic group of C16 within the amphiphilic repeat unit.

PA-14, hydrolyzed, of Comparative Example C2 was obtained by performing a reaction of a 1:1 alternating copolymer of 1-tetradecene and maleic anhydride (PA-14) with sodium hydroxide in aqueous solution to yield a tetradecene/MA copolymer having a weight average of about 50 amphiphilic repeat units, a mole fraction of amphiphilic repeat units of about 100%, and a hydrophobic group of C12 within the amphiphilic repeat unit.

Cetyl Hydroxyethylcellulose of Comparative Example 3 was obtained from Hercules, Inc. of Wilmington, Del. as NATROSOL Plus CS 330.

Sodium Tapioca Dextrin Dodecenylsuccinate, of Inventive Examples E1-E3 was prepared by the process describe below.

A flask equipped with a stirrer, pH probe, and inlet port was charged with 250 g water. To the flask was added a low molecular weight, dry tapioca starch dextrin (125 g) and the pH was adjusted to pH 2 with acid (hydrochloric acid:water in a 3:1 mixture). The reaction mixture was then charged with the reactive anhydride (dodecenylsuccinic anhydride, 12.5 g) and mixed at high speed for one minute. The reaction vessel was then placed in a 40° C. constant temperature bath for the remaining reaction time. The pH of the mixture was adjusted to 8.5 using an aqueous sodium hydroxide solution and held constant at 8.5 for 21 hours. After this time, the reaction was cooled and the pH was adjusted to 7 using acid (hydrochloric acid:water in a 3:1 mixture).

The Sodium Potato Dextrin Dodecenylsuccinates of Inventive Examples E4-E6 was prepared by a similar process as described above for the Sodium Tapioca Dextrin Dodecenylsuccinate, except that the flask was charged with 600 g water, 300 g of a low molecular weight potato starch was added, the reaction mixture was charged with 23 grams of dodecenylsuccinic anhydride. Characterization of ARU, SRU and DP for these inventive examples is shown in Table 1 above.

A representative chemical structure of the inventive sodium dextrin dodecenylsuccinates is shown above in the specification under Subclass (B) of representative SACs.

Comparison of Polymerized Surfactants: The polymerized surfactants prepared in accordance with Examples C1-C3 and E1-E6 were tested for dynamic surface tension reduction in accordance with the above DSA Test. The results of these tests are listed below in Table 2:

TABLE 2

| Example | Description | $t_{\gamma=55}$ |
|---------|-------------|-----------------|
| C1 | hydrolyzed PA-18 (Octadecene/MA Copolymer) | >120 |
| C2 | hydrolyzed PA-14 (Tetradecene/MA Copolymer) | >120 |
| C3 | Natrosol Plus CS 330 (Cetyl Hydroxyethylcellulose) | >120 |
| E1 | Sodium Tapioca Dextrin Dodecenylsuccinate | 35.3 |
| E2 | Sodium Tapioca Dextrin Dodecenylsuccinate | 3.7 |
| E3 | Sodium Tapioca Dextrin Dodecenylsuccinate | <1.0 |
| E4 | Sodium Potato Dextrin Dodecenylsuccinate | 43.0 |
| E5 | Sodium Potato Dextrin Dodecenylsuccinate | 12.7 |
| E6 | Sodium Potato Dextrin Dodecenylsuccinate | 25.2 |

As seen in Table 2, the Dynamic Surface Tension Reduction, specifically, $t_{\gamma=55}$, associated with the comparative examples, C1-C3 is greater than 120 seconds. The $t_{\gamma=55}$ for the inventive examples, E1-E6 is less than one quarter of those of the comparative examples, indicating the SACs useful in the present invention are capable of providing rapidly developing foam.

Comparison of Polymerized Surfactants: The polymerized surfactants prepared in accordance with Examples C1-C3 and E1-E6 were tested for solution viscosity in accordance with the above Solution Viscosity Test. The results of these tests are listed below in Table 3:

TABLE 3

| Example | Description | Solution viscosity (cP) |
|---------|-------------|-------------------------|
| C1 | hydrolyzed PA-18 (Octadecene/MA Copolymer) | 0.85 |
| C2 | hydrolyzed PA-14 (Tetradecene/MA Copolymer) | 0.84 |
| C3 | Natrosol Plus CS 330 (Cetyl Hydroxyethylcellulose) | 8227 |
| E1 | Sodium Tapioca Dextrin Dodecenylsuccinate | 0.91 |
| E2 | Sodium Tapioca Dextrin Dodecenylsuccinate | 0.91 |
| E3 | Sodium Tapioca Dextrin Dodecenylsuccinate | 0.90 |
| E4 | Sodium Potato Dextrin Dodecenylsuccinate | 0.95 |
| E5 | Sodium Potato Dextrin Dodecenylsuccinate | 0.94 |
| E6 | Sodium Potato Dextrin Dodecenylsuccinate | 0.92 |

As seen in Table 3, the Solution Viscosity, associated with the Inventive examples, E1-E6 is for all of the examples tested, below 1 cP. The polymerized surfactant of Comparative example C3, however, causes a dramatic increase in solution viscosity, which can result in unsuitability for foaming cleansers.

Comparison of Polymerized Surfactants: The polymerized surfactants prepared in accordance with Examples C1-C3 and E1-E6 were tested for foam in accordance with the above Polymer Foam Test. The results of these tests are listed below in Table 4:

TABLE 4

| Example | Description | Max Foam Volume (mL) |
|---------|-------------|----------------------|
| C1 | hydrolyzed PA-18 (Octadecene/MA Copolymer) | 87 |
| C2 | hydrolyzed PA-14 (Tetradecene/MA Copolymer) | 59 |
| C3 | Natrosol Plus CS 330 (Cetyl Hydroxyethylcellulose) | 402 |
| E1 | Sodium Tapioca Dextrin Dodecenylsuccinate | 718 |
| E2 | Sodium Tapioca Dextrin Dodecenylsuccinate | 745 |
| E3 | Sodium Tapioca Dextrin Dodecenylsuccinate | 734 |
| E4 | Sodium Potato Dextrin Dodecenylsuccinate | 469 |
| E5 | Sodium Potato Dextrin Dodecenylsuccinate | 452 |
| E6 | Sodium Potato Dextrin Dodecenylsuccinate | 773 |

As seen in Table 4, the Foam Volume as determined by the Polymer Foam Test, for Inventive examples, E1-E6 is greater than 100 mL, whereas Comparative examples C1 and C2 is considerably lower. It can also be seen that the compositions that include SACs are also capable of providing a high level of foam, despite the absence of monomeric surfactant. The foam volume shown by C1 and C2 can, in use, result in the need to add additional foaming agents in order to meet the foaming requirements of the end user. This can cause an undesirable increase in raw material costs.

Examples E7-E12 and Comparative Examples C4-C5

Preparation of Model Compositions for Dynamic Light Scattering Test

Model compositions of Inventive Examples E7 through E12 as well as Comparative Examples C4 and C5 were prepared in order to perform the DLS test. The model compositions were prepared by separately blending the particular polymerized surfactants shown above with other ingredients as follows: Water (about 50.0 parts) was added to a beaker fitted with a mechanical stirrer and hotplate. Sodium Methylparaben (and) Sodium Propylparaben (and) Sodium Ethylparaben (Nipasept Sodium, Clariant Corp.) powder was added and mixed until dissolved. The polymerized surfactant was then added at low stir speed, to avoid aeration. Tetrasodium EDTA (Versene XL, Dow Chemical) was added and mixing was continued. Heat was provided (no greater than 60° C.) if necessary to obtain a uniform solution. The batch was allowed to cool to 25° C. if necessary, while mixing was continued at medium speed. pH was adjusted to 7.0±0.2 using citric acid or sodium hydroxide solution. Water was added to q.s. to 100%. The model compositions are shown in Table 5, below:

Comparison of Model Compositions: The model compositions prepared in accordance with Examples C1-C3 and E1-E6 were tested for dynamic light scattering in accordance with the above DLS Test. The results of these tests are listed below in Table 6:

TABLE 6

| Example | Description | Z-Average Micelle $d_H$ (nm), PMOD z-average | Fraction of micelles with $d_H$ < 9 nm, PMOD % |
|---|---|---|---|
| C4 | hydrolyzed PA-18 (Octadecene/MA Copolymer) | 15.1 | 10.0 |
| C5 | hydrolyzed PA-14 (Tetradecene/MA Copolymer) | 48.6 | 4.0 |
| C6 | Natrosol Plus CS 330 (Cetyl Hydroxyethylcellulose) | — | — |

TABLE 5

| Polymerized Surfactant | INCI Name | C4 | C5 | E7 | E8 | E9 | E10 | E11 | E12 |
|---|---|---|---|---|---|---|---|---|---|
| C1 | Octadecene/MA Copolymer | 18.46 | — | — | — | — | — | — | — |
| C2 | Tetradecene/MA Copolymer | — | 18.46 | — | — | — | — | — | — |
| E1 | Sodium Tapioca Dextrin Dodecenylsuccinate (prop.) | — | — | 5.05 | — | — | — | — | — |
| E2 | Sodium Tapioca Dextrin Dodecenylsuccinate (prop.) | — | — | — | 5.05 | — | — | — | — |
| E3 | Sodium Tapioca Dextrin Dodecenylsuccinate (prop.) | — | — | — | — | 5.05 | — | — | — |
| E4 | Sodium Potato Dextrin Dodecenylsuccinate (prop.) | — | — | — | — | — | 5.05 | — | — |
| E5 | Sodium Potato Dextrin Dodecenylsuccinate (prop.) | — | — | — | — | — | — | 5.05 | — |
| E6 | Sodium Potato Dextrin Dodecenylsuccinate (prop.) | — | — | — | — | — | — | — | 5.05 |
| Nipasept Sodium | Sodium Methylparaben (and) Sodium Propylparaben (and) Sodium Ethylparaben | 0.30 | 0.30 | 0.30 | 0.30 | 0.30 | 0.30 | 0.30 | 0.30 |
| Versene 100XL (50%) | Tetrasodium EDTA | 0.25 | 0.25 | 0.25 | 0.25 | 0.25 | 0.25 | 0.25 | 0.25 |
| Sodium Hydroxide solution (20%) | Sodium Hydroxide | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. |

TABLE 6-continued

| Example | Description | Z-Average Micelle $d_H$ (nm), PMOD z-average | Fraction of micelles with $d_H$ < 9 nm, PMOD % |
|---|---|---|---|
| E7 | Sodium Tapioca Dextrin Dodecenylsuccinate | 6.51 | 69.8 |
| E8 | Sodium Tapioca Dextrin Dodecenylsuccinate | 16.9 | 30.1 |
| E9 | Sodium Tapioca Dextrin Dodecenylsuccinate | — | — |
| E10 | Sodium Potato Dextrin Dodecenylsuccinate | 12.7 | 29.1 |
| E11 | Sodium Potato Dextrin Dodecenylsuccinate | 30.1 | 11.5 |
| E12 | Sodium Potato Dextrin Dodecenylsuccinate | 8.92 | 42.3 |

Table 6 indicates that the Inventive examples, E1-E6 provide a fraction of small micelles (as indicated by PMOD %) that is surprisingly low, i.e., <90%. This is suggestive that the inventive examples will desirably provide low irritation.

Inventive Examples E13-E16 and Comparative Examples C7-C8

Preparation of Inventive and Comparative Examples

Preparation of Inventive Examples E13-E16: Liquid cleanser formulations (shown in Table 7 below) were prepared as follows: To a beaker fitted with a mechanical stirrer and hotplate were added water (about 40.0 parts) and Glycerin. Mixing at low-medium speed and heating to 75° C. were commenced. The example SAC polymer was then added. (Note: In the case of Comparative Example polymers C1 and C2, 11.25 parts of 20% Sodium Hydroxide solution were added to facilitate hydrolysis in situ.) As the batch reached 60° C., PEG-120 Methyl Glucose Dioleate was added. The batch was allowed to mix at 75° C. until all solids were dissolved and the batch was uniform. Heating was then stopped and the batch allowed to cool to ca. 50° C., at which point Cocamidopropyl Betaine was added. Upon cooling to below 40° C., Tetrasodium EDTA, DMDM Hydantoin, and Fragrance were added. In a separate vessel, Polyquaternium-10 and Water (15.0 parts) were combined and mixed until completely dissolved; this mixture was then added to the main batch. The batch was allowed to cool to 25° C. if necessary, while mixing was continued at medium speed. pH was adjusted to 7.0±0.2 using citric acid or sodium hydroxide solution. Water was added to q.s. to 100%.

In the case of Comparative Examples C7 and C8, a modified procedure was employed as follows: To a beaker fitted with a mechanical stirrer and hotplate was added water (about 40.0 parts) Mixing at low-medium speed and heating to 90° C. were commenced. The comparative example polymer was then added. To facilitate in situ hydrolysis, 11.25 parts of 20% Sodium Hydroxide solution was added, and the batch mixed at 90° C. until the polymer was completely dissolved, at which point heating was stopped. Upon cooling to 75° C., PEG-120 Methyl Glucose Dioleate was added. The batch was allowed to mix at 75° C. until all solids were dissolved and the batch was uniform. Heating was then stopped and the batch allowed to cool to ca. 50° C., at which point Cocamidopropyl Betaine was added. Upon cooling to below 40° C., Tetrasodium EDTA, DMDM Hydantoin, and Fragrance were added. In a separate vessel, Polyquaternium-10 and Water (15.0 parts) were combined and mixed until completely dissolved; this mixture was then added to the main batch. The batch was allowed to cool to 25° C. if necessary, while mixing was continued at medium speed. pH was adjusted to 7.0±0.2 using citric acid or sodium hydroxide solution. Water was added to q.s. to 100%.

TABLE 7

| Polymerized Surfactant | INCI Name | C7 | C8 | E13 | E14 | E15 | E16 |
|---|---|---|---|---|---|---|---|
| C1 | Octadecene/MA Copolymer | 9.00 | — | — | — | — | — |
| C2 | Tetradecene/MA Copolymer | — | 9.00 | — | — | — | — |
| E2 | Sodium Tapioca Dextrin Dodecenylsuccinate (prop.) | — | — | 9.00 | — | — | — |
| E4 | Sodium Potato Dextrin Dodecenylsuccinate (prop.) | — | — | — | 9.00 | — | — |
| E5 | Sodium Potato Dextrin Dodecenylsuccinate (prop.) | — | — | — | — | 9.00 | — |
| E6 | Sodium Potato Dextrin Dodecenylsuccinate (prop.) | — | — | — | — | — | 9.00 |
| Tegobetaine L7-V (30%) | Cocamidopropyl Betaine | 7.00 | 7.00 | 7.00 | 7.00 | 7.00 | 7.00 |
| Emery 917 | Glycerin | 5.00 | 5.00 | 5.00 | 5.00 | 5.00 | 5.00 |
| Glucamate DOE-120 | PEG-120 Methyl Glucose Dioleate | 7.00 | 7.00 | 7.00 | 7.00 | 7.00 | 7.00 |
| Versene 100XL (50%) | Tetrasodium EDTA | 1.00 | 1.00 | 1.00 | 1.00 | 1.00 | 1.00 |
| Glydant (55%) | DMDM Hydantoin | 0.50 | 0.50 | 0.50 | 0.50 | 0.50 | 0.50 |
| Polymer JR400 | Polyquaternium-10 | 0.15 | 0.15 | 0.15 | 0.15 | 0.15 | 0.15 |
| Fragrance | Fragrance | 0.20 | 0.20 | 0.20 | 0.20 | 0.20 | 0.20 |
| Sodium Hydroxide solution (20%) | Sodium Hydroxide | q.s. | q.s. | q.s. | q.s. | q.s. | q.s. |

TABLE 7-continued

| Polymerized Surfactant | INCI Name | C7 | C8 | E13 | E14 | E15 | E16 |
|---|---|---|---|---|---|---|---|
| Citric Acid solution (20%) | Citric Acid | q.s. | q.s. | q.s. | q.s. | q.s. | q.s. |
| Purified Water | Water | q.s. | q.s. | q.s. | q.s. | q.s. | q.s. |

Comparison of Compositions: The compositions prepared in accordance with Examples C7-C8 and E13-E16 were tested for foam in accordance with the above Formulation Foam Test. The results of these tests are listed below in Table 8:

TABLE 8

| Example | Max Foam Volume (mL) |
|---|---|
| C7 | 78 |
| C8 | 73 |
| E13 | 267 |
| E14 | 246 |
| E15 | 227 |
| E16 | 267 |

As seen in Table 8, the foam associated with the Inventive examples, E13-E16 is considerably higher (about triple) than those measured for comparative examples C7 and C8.

Inventive Examples E17-E20

Preparation and Testing of Inventive Examples

The QUAB® 342 (quat reagent) modified potato dextrin polymers of E17-E20 were prepared by charging a flask equipped with a stirrer, pH probe, and inlet port with 600 g water. To the flask dry potato starch dextrin (300 g) was added. Also, 2.4 grams of sodium hydroxide was added as a 3% aqueous solution (80 mLs) at the rate of 7.5 mls/minute. The reaction was then heated to 43° C. and allowed to stir for 30 minutes at temperature. Approximately ½ the total amount of sodium hydroxide needed to neutralize the quat reagent was added at 7.5 mls/minute. The total active charge of QUAB® 342 quat reagent (30 grams for E17, 6 grams for E18, 60 grams for E19, and 90 grams for E20) was added by pouring the reagent into the reaction vessel with agitation. The remainder of the sodium hydroxide was then added at 7.5 mls/minutes until the pH of the reaction was at or slightly above 11.5. The reaction was stirred overnight at 43° C. (approximately 18 hours) and then cooled to room temperature (25° C.). The pH was adjusted to 5.5 using dilute (10%) hydrochloric acid and the product was recovered by precipitating into isopropyl alcohol. The powder was washed three times with 500 mls of isopropyl alcohol and then air dried. The total bound nitrogen for E17-E20 was 0.28% for E17, 0.10% for E18, 0.38% for E19, and 0.53% for E20.

TABLE 9

| Example | Description | total #RU ("DP") | mol % ARU | avg # ARU (a) | avg # SRU (s) |
|---|---|---|---|---|---|
| E17 | Laurdimonium Hydroxypropyl Potato Dextrin Chloride | 33 | 3.4 | 1.1 | 32 |
| E18 | Laurdimonium Hydroxypropyl Potato Dextrin Chloride | 33 | 1.2 | 0.4 | 33 |
| E19 | Laurdimonium Hydroxypropyl Potato Dextrin Chloride | 33 | 4.8 | 1.6 | 31 |
| E20 | Laurdimonium Hydroxypropyl Potato Dextrin Chloride | 33 | 6.9 | 2.3 | 31 |

The polymerized surfactants prepared in accordance with Examples E17-E20 were tested for dynamic surface tension reduction in accordance with the above DSA Test. The results of these tests are listed below in Table 10:

TABLE 10

| Example | Description | $t_{\gamma-55}$ |
|---|---|---|
| E17 | Laurdimonium Hydroxypropyl Potato Dextrin Chloride | >120 |
| E18 | Laurdimonium Hydroxypropyl Potato Dextrin Chloride | >120 |
| E19 | Laurdimonium Hydroxypropyl Potato Dextrin Chloride | >120 |
| E20 | Laurdimonium Hydroxypropyl Potato Dextrin Chloride | >120 |

The polymerized surfactants prepared in accordance with Examples E17-E20 were tested for foam in accordance with the above Polymer Foam Test. The results of these tests are listed below in Table 11:

TABLE 11

| Example | Description | Max Foam Volume (mL) |
|---|---|---|
| E17 | Laurdimonium Hydroxypropyl Potato Dextrin Chloride | 369 |
| E18 | Laurdimonium Hydroxypropyl Potato Dextrin Chloride | 30 |
| E19 | Laurdimonium Hydroxypropyl Potato Dextrin Chloride | 542 |
| E20 | Laurdimonium Hydroxypropyl Potato Dextrin Chloride | 758 |

Compositions E21-E24 and DLS Testing Thereof:

Model compositions of Inventive Examples E21-E24 were prepared in order to perform the DLS test. The model compositions were prepared by separately blending the particular polymerized surfactants shown above with other ingredients as follows: Water (about 50.0 parts) was added to a beaker fitted with a mechanical stirrer and hotplate. Sodium Methylparaben (and) Sodium Propylparaben (and) Sodium Ethylparaben (Nipasept Sodium, Clariant Corp.) powder was added and mixed until dissolved. The polymerized surfactant was then added at low stir speed, to avoid aeration. Tetrasodium EDTA (Versene XL, Dow Chemical) was added and mixing was continued. Heat was provided (no greater than 60° C.) if necessary to obtain a uniform solution. The batch was allowed to cool to 25° C. if necessary, while mixing was continued at medium speed. pH was adjusted to 7.0±0.2 using citric acid or sodium hydroxide solution. Water was added to q.s. to 100%. The model compositions are shown in Table 12, below:

TABLE 12

| Polymerized Surfactant | INCI Name | E21 | E22 | E23 | E24 |
|---|---|---|---|---|---|
| E17 | Laurdimonium Hydroxypropyl Potato Dextrin Chloride (prop.) | 5.05 | — | — | — |
| E18 | Laurdimonium Hydroxypropyl Potato Dextrin Chloride (prop.) | — | 5.05 | — | — |
| E19 | Laurdimonium Hydroxypropyl Potato Dextrin Chloride (prop.) | — | — | 5.05 | — |
| E20 | Laurdimonium Hydroxypropyl Potato Dextrin Chloride (prop.) | — | — | — | 5.05 |
| Niapsept Sodium | Sodium Methyl Paraben (and) Sodium Propylparaben (and) Sodium Ethylparaben | 0.30 | 0.30 | 0.30 | 0.30 |
| Versene 100XL (50%) | Tetrasodium EDTA | 0.25 | 0.25 | 0.25 | 0.25 |
| Sodium Hydroxide soluton (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |

The model compositions prepared in accordance with Examples E21-E24 were tested for dynamic light scattering in accordance with the above DLS Test. The results of these tests are listed below in Table 13:

TABLE 13

| Example | Description | Z-Average Micelle $d_H$ (nm), PMOD z-average | Fraction of micelles with $d_H$ < 9 nm, PMOD % |
|---|---|---|---|
| E21 | Laurdimonium Hydroxypropyl Potato Dextrin Chloride | 11.5 | 32.1 |
| E22 | Laurdimonium Hydroxypropyl Potato Dextrin Chloride | 12.0 | 36.1 |
| E23 | Laurdimonium Hydroxypropyl Potato Dextrin Chloride | 11.1 | 31.5 |
| E24 | Laurdimonium Hydroxypropyl Potato Dextrin Chloride | 10.1 | 36.4 |

Examples E25-E32

Preparation of Inventive Personal Care Compositions and Measurement of Formulation Viscosity The following personal care compositions, Inventive Examples E25-E32, and were prepared and tested for Formulation Viscosity. Each of Inventive Examples E25-E32 included a SAC and a corona thickener.

TABLE 14

| Tradename | INCI Name | E25 | E26 | E27 | E28 | E29 | E30 | E31 | E32 |
|---|---|---|---|---|---|---|---|---|---|
| HM Starch Slurry (29%) | Sodium Dextrin Dodecenylsuccinate (prop.) | 31.64 | 31.64 | 31.64 | 31.64 | 31.64 | 31.64 | 31.64 | 31.64 |
| Tegobetaine L7-V (30%) | Cocamidopropyl Betaine | 7.00 | 7.00 | 7.00 | 7.00 | 7.00 | 7.00 | 7.00 | 7.00 |
| Emery 917 | Glycerin | 5.00 | 5.00 | 5.00 | 1.75 | 5.00 | 5.00 | 5.00 | 5.00 |
| Ethox PEG 6000 DS Special | PEG-150 Distearate | 1.40 | 1.60 | — | — | — | — | — | — |
| Glucamate DOE-120 | PEG-120 Methyl Glucose Dioleate | — | — | 6.10 | — | — | — | — | — |
| Glucamate LT | PEG-120 Methyl Glucose Trioleate (and) Propylene Glycol (and) Water | — | — | — | 10.0 | — | — | — | — |
| Ethox HVB | PEG-175 Diisostearate | — | — | — | — | — | 1.75 | — | — |
| Ethox NED-2 | Decyltetradeceth-200 Dimerate | — | — | — | — | — | — | 1.40 | — |
| Ethox NEBS-2 | Decyltetradeceth-200 Behenate | — | — | — | — | — | — | 1.28 | — |
| Ethox PEG 6000 DB | PEG-150 Dibehenate | — | — | — | — | — | — | — | 1.85 |
| Versene 100XL (50%) | Tetrasodium EDTA | 1.00 | 1.00 | 1.00 | 1.00 | 1.00 | 1.00 | 1.00 | 1.00 |
| Glydant (55%) | DMDM Hydantoin | 0.50 | 0.50 | 0.50 | 0.50 | 0.50 | 0.50 | 0.50 | 0.50 |

TABLE 14-continued

| Tradename | INCI Name | E25 | E26 | E27 | E28 | E29 | E30 | E31 | E32 |
|---|---|---|---|---|---|---|---|---|---|
| Fragrance | Fragrance | 0.20 | 0.20 | 0.20 | 0.20 | 0.20 | 0.20 | 0.20 | 0.20 |
| Sodium Hydroxide solution (20%) | Sodium Hydroxide | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. |
| | Viscosity (cP) | 226.5 | 1734 | 3427 | 2930 | 2090 | 1015 | 2380 | 4190 |

Sodium Tapioca Dextrin Dodecenylsuccinate, of Inventive Examples E25-E32 was prepared by the process describe below.

A flask equipped with a stirrer, pH probe, and inlet port was charged with 250 g water. To the flask was added a low molecular weight, dry tapioca starch dextrin (125 g) and the pH was adjusted to pH 2 with acid (hydrochloric acid:water in a 3:1 mixture). The reaction mixture was then charged with the reactive anhydride (dodecenylsuccinic anhydride, 12.5 g) and mixed at high speed for one minute. The reaction vessel was then placed in a 40° C. constant temperature bath for the remaining reaction time. The pH of the mixture was adjusted to 8.5 using an aqueous sodium hydroxide solution and held constant at 8.5 for 21 hours. After this time, the reaction was cooled and the pH was adjusted to 7 using acid (hydrochloric acid:water in a 3:1 mixture).

Inventive Example, Ex. 25 was prepared as follows: to an appropriately sized vessel equipped with a hotplate and overhead mechanical stirrer, 60 parts Water was added. While mixing at 200-250 rpm and heating to 85-90° C., Glycerin and Sodium Dextrin Dodecenylsuccinate slurry were added. At 65° C., PEG-150 Distearate was added. The batch was mixed at 85-90° C. until all PEG-150 Distearate was dissolved. Upon complete dissolution of all PEG-150 Distearate, heating was stopped and the batch was allowed to cool to 50° C. while mixing at 200-250 rpm. At 50° C., Cocamidopropyl Betaine was added to the batch, and the batch was allowed to cool below 40° C., at which point Tetrasodium EDTA, DMDM Hydantoin, and Fragrance were added. The batch was allowed to mix while cooling to below 30° C. and was then adjusted to pH 6.7-7.2 (target pH=6.9) using necessary amounts of Citric Acid and/or Sodium Hydroxide. Water was added in q.s. to 100 wt %, and the batch was allowed to mix until uniform before being discharged to an appropriate storage vessel. Inventive Examples Ex. 26-Ex. 32 were prepared in a similar manner. Formulation Viscosity was measured for each of the Inventive Examples using the Formulation Viscosity Test described above. Formulation Viscosity (in centipoise, cP) is reported in Table 14.

As is apparent from Table 14, a variety of micellar thickeners can be combined with Sodium Dextrin Dodecenylsuccinate (a SAC) to achieve viscosities that vary from, for example as low as 226 cP to as high as 4190 cP.

Characterization of the SAC of E13-E28 and C7 (HM Slurry) shows that it has total of 37 RUs with a mol % ARU of 6.1, which breaks down to an average of 2.3 ARUs (a) and 35 SRUs (s). The $t_{y=55}$ for this sample is greater than 120 seconds. The solution viscosity for the sample is <2 cP (estimated according to DP). The maximum foam volume for the sample is 195 mL. When made using the procedures in the Preparation of Model Compositions for Dynamic Light Scattering Test, the Z-Average Micelle $d_H$ is 15.2 nm and the fraction of micelles with $d_H$ is 34.7%.

Examples E33-E36

Preparation of Inventive Personal Care Compositions and Measurement of Formulation Viscosity The following personal care compositions, Inventive Examples E-E36 and were prepared and tested for Formulation Viscosity.

TABLE 8

| Tradename | INCI Name | E33 | E34 | E35 | E36 |
|---|---|---|---|---|---|
| HM Starch Slurry (29%) | Sodium Dextrin Dodecenylsuccinate (prop.) | 31.64 | 31.64 | 31.64 | 31.64 |
| Tegobetaine L7-V (30%) | Cocamidopropyl Betaine | 7.00 | 7.00 | 7.00 | 7.00 |
| Emery 917 | Glycerin | 5.00 | 5.00 | 5.00 | 5.00 |
| Glucamate DOE-120 | PEG-120 Methyl Glucose Dioleate | 3.00 | 6.10 | 7.00 | 8.50 |
| Versene 100XL (50%) | Tetrasodium EDTA | 1.00 | 1.00 | 1.00 | 1.00 |
| Glydant (55%) | DMDM Hydantoin | 0.50 | 0.50 | 0.50 | 0.50 |
| Fragrance | Fragrance | 0.20 | 0.20 | 0.20 | 0.20 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |
| | Viscosity (cP) | 36.9 | 3427 | 3712 | 8325 |

Inventive Examples, Ex. 33-Ex. 36 were prepared in a manner similarly to Inventive Examples Ex. 13-Ex. 20. As is apparent from Table 14, by increasing the concentration of PEG-120 Methyl Glucose Dioleate, one is able to increase the viscosity of a composition that includes Sodium Dextrin Dodecenylsuccinate from, for example, about 37 cP to about 8325 cP.

Examples E37-E40

Preparation of Inventive Personal Care Compositions and Measurement of Formulation Viscosity The following personal care compositions, Inventive Examples E37-E40 and were prepared and tested for Formulation Viscosity.

TABLE 15

| Tradename | INCI Name | E37 | E38 | E39 | E40 |
|---|---|---|---|---|---|
| HM Starch Slurry (29%) | Sodium Dextrin Dodecenylsuccinate (prop.) | 31.64 | 31.64 | 31.64 | 31.64 |
| Tegobetaine L7-V (30%) | Cocamidopropyl Betaine | 7.00 | 7.00 | 7.00 | 7.00 |
| Emery 917 | Glycerin | 5.00 | 5.00 | 5.00 | 5.00 |
| Ethox PEG 6000 DS Special | PEG-150 Distearate | 1.40 | 1.60 | 1.80 | 1.90 |
| Versene 100XL (50%) | Tetrasodium EDTA | 1.00 | 1.00 | 1.00 | 1.00 |
| Glydant (55%) | DMDM Hydantoin | 0.50 | 0.50 | 0.50 | 0.50 |
| Fragrance | Fragrance | 0.20 | 0.20 | 0.20 | 0.20 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |
|  | Viscosity (cP) | 226.5 | 1734 | 2892 | 4245 |

Inventive Examples, Ex. 37-Ex. 40 were prepared in a manner similarly to Inventive Examples Ex. 33-Ex. 36, but using a different micellar thickener. As is apparent from Table 15, by increasing the concentration of PEG-150 Distearate, one is also able to increase the viscosity of the composition that includes Sodium Dextrin Dodecenylsuccinate from, for example, about 226 cP to about 4245 cP. Similarly to Inventive Examples Ex. 33-Ex. 36, the increase in Formulation Viscosity is highly non-linear with respect to concentration of micellar thickener.

Comparative Example C8

Preparation of Comparative Personal Care Compositions and Measurement of Formulation Viscosity The following personal care composition, Comparative Example C8 was prepared and tested for Formulation Viscosity.

TABLE 16

| Tradename | INCI Name | C8 |
|---|---|---|
| HM Starch Slurry (29%) | Sodium Starch Dodecenylsuccinate (prop.) | 31.64 |
| Tegobetaine L7-V (30%) | Cocamidopropyl Betaine | 7.00 |
| Emery 917 | Glycerin | 5.00 |
| Carbopol AQUA SF-1 (30%) | Acrylates Copolymer | 7.00 |

TABLE 16-continued

| Tradename | INCI Name | C8 |
|---|---|---|
| Versene 100XL (50%) | Tetrasodium EDTA | 1.00 |
| Glydant (55%) | DMDM Hydantoin | 0.50 |
| Fragrance | Fragrance | 0.20 |
| Sodium Hydroxide solution (20%) | Sodium Hydroxide | q.s. |
| Citric Acid solution (20%) | Citric Acid | q.s. |
| Purified Water | Water | q.s. |
|  | Viscosity (cP) | 4875 |

Comparative Example, C8 was prepared in a similar manner to the previous Inventive Example, Ex. 35, except that Carbopol Aqua SF-1 (a conventional, high molecular weight, "alkali-swellable emulsion polymeric thickener") was substituted for PEG-120 Methyl Glucose Dioleate. The Formulation Viscosity was measured to be 4875 cP (reasonably close to Inventive Example, Ex. 35).

Comparison of Formulation Flash Foam Values for Personal Care Compositions

Inventive Example, Ex. 35 and Comparative Example C8 were tested for Formulation Flash Foam Value using the Formulation Flash Foam Test described above. The data is shown in Table 17 below. The two data sets (one for Comparative Example C8 and the other for Inventive Example, Ex. 35) are also shown in FIG. 1.

TABLE 17

| | Foam Volume of C7 (mL) | | | | Foam Volume of E23 (mL) | | | |
|---|---|---|---|---|---|---|---|---|
| Cycles | Run 1 | Run 2 | Avg | Std Dev | Run 1 | Run 2 | Avg | Std Dev |
| 2 | 145 | 125 | 135 | 14 | 130 | 135 | 133 | 4 |
| 4 | 165 | 150 | 158 | 11 | 160 | 160 | 160 | 0 |
| 6 | 200 | 175 | 188 | 18 | 200 | 240 | 220 | 28 |
| 8 | 225 | 200 | 213 | 18 | 250 | 250 | 250 | 0 |
| 10 | 225 | 225 | 225 | 0 | 300 | 300 | 300 | 0 |
| 12 | 250 | 240 | 245 | 7 | 350 | 350 | 350 | 0 |
| 14 | 250 | 250 | 250 | 0 | 400 | 400 | 400 | 0 |
| 16 | 270 | 260 | 265 | 7 | 450 | 450 | 450 | 0 |
| 18 | 280 | 265 | 273 | 11 | 500 | 500 | 500 | 0 |
| 20 | 290 | 275 | 283 | 11 | 525 | 520 | 523 | 4 |

As can be readily seen in Table 17, Inventive Example, Ex. 35 essentially develops greater flash foam, e.g., a higher amount of foam than Comparative Example, C8, when compared at most points (number of cycles) during the test. Inventive Example, Ex. 35 also reaches a terminal foam volume at 20 cycles that is 84% higher than that of Comparative Example, C8 (523 compared with 283).

Furthermore, as can be seen in FIG. 1, the Foam Generation Rate, FGR, for Inventive Example, Ex. 35 is almost triple that of Comparative Example, C8 (22.84 compared with 8.04). Applicants attribute this superiority in performance of the Inventive Examples to the dramatic improvement in the micellar thickener-thickened formula to "break" and lose viscosity upon dilution. By comparison, the SAC-containing compositions that are thickened with the conventional high molecular weight alkali-swellable emulsion polymeric thickeners do not readily "break" upon dilution and are relatively poor flash foamers.

The following Examples are included to illustrate the effect molecular weight, differing amounts of hydrophobic reagents and the use of different starch-based SACs on clarity, viscosity, foam generation and foam stability as it relates to the present invention.

Example 41

The Preparation of an Aqueous Solution of Native (Unmodified) Tapioca Starch

An aqueous solution of native (unmodified) tapioca was prepared by suspending 10 g dry native tapioca starch in 200 g water. The mixture was heated at 80° C. with stirring for 30 minutes. The resulting thick and translucent solution was allowed to cool.

Example 42

The Preparation of an Aqueous Solution of a Tapioca Starch Dextrin

An aqueous solution of tapioca starch dextrin was prepared by suspending 10 g tapioca dextrin in 100 g water. The suspension was mixed without heating until the power dissolved. The resulting solution was slightly hazy.

Example 43

The Preparation of an Aqueous Solution of a Dodecenylsuccinic Anhydride Modified Tapioca Starch Dextrin An aqueous solution of a dodecenylsuccinic anhydride modified tapioca starch dextrin was prepared by charging a flask equipped with a stirrer, pH probe, and inlet port with 250 g water. To the flask, dry tapioca starch dextrin (125 g) was added and the pH was adjusted to a pH of 2 with acid (hydrochloric acid:water in a 3:1 mixture). The reaction mixture was then charged with the reactive anhydride (dodecenylsuccinic anhydride, 12.5 g) and mixed at high speed for one minute. The reaction vessel was then placed in a 40° C. constant temperature bath for the remaining reaction time. The pH of the mixture was adjusted to 8.5 using an aqueous sodium hydroxide solution and held constant at 8.5 for 21 hours. After this time, the reaction was cooled and the pH adjusted to 7 using acid (hydrochloric acid:water in a 3:1 mixture). It should be noted that the starch solution prepared according to this example can either be used immediately or stored for future use. If it is stored, it must be refrigerated, preserved, or spray dried.

Example 44

The Preparation of an Aqueous Solution of a Octenylsuccinic Anhydride (OSA) Modified Potato Starch Dextrin An aqueous solution of octenylsuccinic anhydride (OSA) was prepared by charging a flask equipped with a stirrer, pH probe, and inlet port with 600 g water. To the flask dry tapioca starch dextrin (300 g) was added and the pH was adjusted to a pH of 2 with acid (hydrochloric acid:water in a 3:1 mixture). The reaction mixture was then charged with the reactive anhydride (octenylsuccinic anhydride, 23 g) and mixed at high speed for one minute. The reaction vessel was then placed in a 40° C. constant temperature bath for the remaining reaction time. The pH of the mixture was adjusted to 8.5 using an aqueous sodium hydroxide solution and held constant at 8.5 for 21 hours. After this time, the pH was adjusted to 7 using acid (hydrochloric acid:water in a 3:1 mixture). It should be noted that the starch solution prepared according to this example can either be used immediately or stored for future use. If it is stored, it must be refrigerated, preserved, or spray dried.

Example 45

Preparation of QUAB® 342 Modified Potato Dextrin Samples

A QUAB® 342 modified potato dextrin was prepared by charging a flask equipped with a stirrer, pH probe, and inlet port with 600 g water. To the flask dry potato starch dextrin (300 g) was added. Also, 2.4 grams of sodium hydroxide was added as a 3% aqueous solution (80 mLs) at the rate of 7.5 mls/minute. The reaction was then heated to 43° C. and allowed to stir for 30 minutes at temperature. Approximately ½ the total amount of sodium hydroxide needed to neutralize the quat reagent was added at 7.5 mls/minute. The total charge of quat (30 grams active reagent, 10% by weight active reagent based on starch) was added by pouring the reagent into the reaction vessel with agitation. The remainder of the sodium hydroxide was then added at 7.5 mls/minutes until the pH of the reaction was at or slightly above 11.5. The reaction was stirred overnight at 43° C. (approximately 18 hours) and then cooled to room temperature (25° C.). The pH was adjusted to 5.5 using dilute (10%) hydrochloric acid and the product was recovered by precipitating into isopropyl alcohol. The powder was washed three times with 500 mls of isopropyl alcohol and then air dried. The bound nitrogen was found to be 0.28 percent, as reported for Sample 13. Samples 14 and 15 were prepared according to the procedure above, except that the amount of active quat charged to the reaction was 20% and 30%, respectively.

Example 46

Clarity in Water

Sample 1 was prepared according to Example 41. Sample 2 was prepared according to Example 42. Samples 3-5 and 10 were prepared as in Example 43 using degraded tapioca starches with noted molecular weights. Samples 6 and 8 were prepared as in Example 43 using differing amounts of DDSA. Sample 7 was prepared as in Example 43 using a potato base and increased DDSA. Sample 9 was prepared as in Example 43 using a corn base. Sample 11 was prepared as in Example 43 using a potato base. Sample 12 was prepared according to Example 44. Sample 13, 14 and 15 were prepared using the process of Example 45.

The samples were tested as a 10% solids solution in water. The solution was evaluated visually as opaque (FAIL) or translucent or clear (PASS). The passing samples were then evaluated at 10% solids using a turbidity test (model 2100N Hach laboratory turbidimeter) and the sample clarity categorized as excellent (<=10 ntu), slightly hazy (greater than 10 to 120 ntu inclusive), hazy (greater than 120 ntu to 400 ntu inclusive), or failing (greater than 400 ntu). The results of the test are shown in Table 18.

TABLE 18

| Sample | Hydrophobe level | Mw of polysaccharide | Clarity evaluation | ntu |
|---|---|---|---|---|
| 1 | 0 | >1,000,000 | Fail | Opaque |
| 1 (5% solution) | 0 | >1,000,000 | sl. Hazy | 83 |
| 2 | 0 | 6442 | sl. Hazy | 57 |
| 3 | 5.52 | 6442 | sl. Hazy | 102 |
| 4 | 6.4 | 23170 | Hazy | 157 |
| 5 | 4.6 | 91223 | Fail | Opaque |
| 6 | 0.95 | 6442 | Hazy | 160 |
| 7 | 10.2 | 5425 | Excellent | 5 |
| 8 | 7.79 | 6308 | sl. Hazy | 93 |
| 9 | 1.3 | 7344 | Fail | 562 |
| 10 | 5.33 | 4568 | sl. Hazy | 78 |
| 11 | 4.58 | 5425 | Excellent | 8 |
| 12 | 7.6 (OSA) | 5425 | Excellent | 5 |
| 13 | 0.28N (QUAB) | 5425 | Excellent | 7.43 |
| 14 | 0.38N (QUAB) | 5425 | Excellent | 9.69 |
| 15 | 0.50N (QUAB) | 5425 | sl. Hazy | 11.80 |

This Example shows the effect of molecular weight on the clarity of solution, with the lower molecular weight corresponding to a clearer solution.

Example 47

SAC Viscosity Test (in Water)

A 10% solids solution of each sample in water was prepared. If the solution was noticeably thick (>1000 cps) it failed. Only sample 1 failed. The other samples were tested for Brookfield viscosity with #3 spindle and at 200 rpm. The results are shown in Table 19.

TABLE 19

| Sample | Hydrophobe level | Mw of polysaccharide | Viscosity evaluation | Viscosity (cps) |
|---|---|---|---|---|
| 1 | 0 | >1,000,000 | Fail | NA |
| 1 (5% solution) | 0 | >1,000,000 | Fail | |
| 2 | 0 | 6442 | Pass | 5 |
| 3 | 5.52 | 6442 | Pass | 5 |
| 4 | 6.4 | 23170 | Pass | 5 |
| 5 | 4.6 | 91223 | Pass | 7.5 |
| 6 | 0.95 | 6442 | Pass | 5 |
| 7 | 10.2 | 5425 | Pass | 5 |
| 8 | 7.79 | 6308 | Pass | 7 |
| 9 | 1.3 | 7344 | Pass | 5 |
| 10 | 5.33 | 4568 | Pass | 5 |
| 11 | 4.58 | 5425 | Pass | 25 |
| 12 | 3.8 (OSA) | 5425 | Pass | 25 |

Example 48

Foam Generation in Water

A 10% solids solution of each sample in water was prepared. The samples were screened for foam generation by adding 5 g of solution into a 20 ml scintillation vial, gently shaking ten times, and measuring the foam generated in the headspace above the liquid. If the foam head was greater than or equal to 0.75" the test was noted as PASS, if the foam head was less than 0.75" the test was noted as FAIL.

To distinguish between excellent and good foaming performance the Formulation Foam Test described previously was run. For the test, a solution of the polymer was prepared by dissolving the polymer (5 g) in water (900 g), adding Glydant preservative (3 g) and tetrasodium EDTA (5 g), adjusting the pH to 7.0+/−0.2 with sodium hydroxide (20 wt % in water) and/or citric acid (20 wt. % in water), followed by the addition of water to reach 1000 mL total volume for the test. The test solution was then added to the sample tank of a Sita R-2000 foam tester and run according to the Formulation Foam Test described previously. The Formulation Foam reported in this example was the value at 150 seconds. Those samples exceeding 575 mL of foam volume at that time were designated as "excellent" foaming samples. The results are set forth in Table 20.

TABLE 20

| Sample | Hydrophobe level | Mw of polysaccharide | Foam Generation | Foam height @ 150 seconds |
|---|---|---|---|---|
| 1 | 0 | >1,000,000 | Fail | |
| 2 | 0 | 6442 | Fail | |
| 3 | 5.52 | 6442 | Pass | 450 |
| 4 | 6.4 | 23170 | Pass | 550 |
| 5 | 4.6 | 91223 | Pass | 500 |
| 6 | 0.95 | 6442 | Fail | |
| 7 | 10.2 | 5425 | Pass (excellent) | 750 |
| 8 | 7.79 | 6308 | Pass (excellent) | 600 |
| 9 | 1.3 | 7344 | NA | |
| 10 | 5.33 | 4568 | Pass | 400 |
| 11 | 4.58 | 5425 | Pass | 400 |
| 12 | 3.8 (OSA) | 5425 | Fail | |

Example 49

Foam Stability in Water

A 10% solids solution of each of samples 1-12 in water was prepared. The samples were screened for foam generation as described in Example 48 and then the vials were set aside for four hours. If some foam was still evident in the vial after that time the foam was noted as persistent and rated as a PASS for the foam stability test.

In order to distinguish between good and excellent foam performance, the SITA foam tester was used as in Example 48. The percent of the foam head remaining 1000 seconds after the stirring was removed was used to quantify the foam stability. Those samples having a retention of between 5 and 50 percent were classified as having GOOD foam stability, those with a retention 50 percent and greater were classified as having EXCELLENT foam stability. The results are summarized in Table 21.

TABLE 21

| Sample | Hydrophobe level | Mw of polysaccharide | Foam Stability Screen | Foam retention @ 1000 sec. |
|---|---|---|---|---|
| 1 | 0 | >1,000,000 | NA | |
| 2 | 0 | 6442 | NA | |
| 3 | 5.52 | 6442 | Pass (good) | 15% |
| 4 | 6.4 | 23170 | Pass (good) | 40% |
| 5 | 4.6 | 91223 | Pass (good) | 40% |

TABLE 21-continued

| Sample | Hydrophobe level | Mw of polysaccharide | Foam Stability Screen | Foam retention @ 1000 sec. |
|---|---|---|---|---|
| 6 | 0.95 | 6442 | NA | |
| 7 | 10.2 | 5425 | Pass (excellent) | >90% |
| 8 | 7.79 | 6308 | Pass (excellent) | >80% |
| 9 | 1.3 | 7344 | NA | |
| 10 | 5.33 | 4568 | Pass (good) | 15% |
| 11 | 4.58 | 5425 | Pass (excellent) | >80% |
| 12 | 3.8 (OSA) | 5425 | NA | |

While particular embodiments of the present invention have been illustrated and described herein, the invention is not intended to be limited to the details shown. Rather, various modifications may be made in the details within the range and scope of equivalents of the claims and without departing from the spirit and scope of the invention.

What is claimed is:

1. A method of cleansing or treating a human body comprising applying to the human body a composition comprising (1) a superhydrophilic amphiphilic copolymer; (2) a micellar thickener; and a cosmetically acceptable or a pharmaceutically acceptable carrier,
wherein said superhydrophilic amphiphilic copolymer is laurdimonium hydroxypropyl potato dextrin chloride, and
wherein said micellar thickener is a corona thickener which is a fatty acid polyester of an ethoxylated glucoside.

2. The method of claim 1, wherein said superhydrophilic amphiphilic copolymer has a mole percent of amphiphilic units that is less 10.

3. The method of claim 1, wherein said cosmetically acceptable or said pharmaceutically acceptable carrier is an aqueous carrier.

4. The method of claim 1, wherein the composition has a foam generation rate of at least about 10 mL/cycle, as measured by adding 50 g of the composition and 50 g of deionized water to a mixing cylinder fitted with a stopper and mounted in a vertical rotator assembly of a Gaum Foam Machine, and the cylinder rotated at cycle speed #30 for a total of 20 cycles, and measuring the height of the foam at the level where the foam bubbles and renders the mixing cylinder opaque, where the foam generation rate is calculated by plotting the height of the foam as a function of shake cycle ranging from 2 cycles to 20 cycles) and calculating the slope of the resulting linear fit.

5. The method of claim 1, wherein said composition is in the form of a shampoo, wash, bath additive, gel, lotion, or cream.

6. The method of claim 1, wherein said composition further comprises an active for treating skin condition selected from the group consisting of acne, wrinkles, dermatitis, dryness, muscle pain, itch, or combinations of two or more thereof.

7. The method of claim 1, wherein said composition is applied to human skin, hair, or vaginal region.

* * * * *